(12) United States Patent
Marczyk et al.

(10) Patent No.: US 10,912,564 B2
(45) Date of Patent: Feb. 9, 2021

(54) MULTI-FIRE PUSH ROD STAPLING DEVICE

(71) Applicant: Covidien LP, Mansfield, MA (US)

(72) Inventors: Stanislaw Marczyk, Stratford, CT (US); Simon R. Grover, Cambridge (GB); Alistair Ward, Cambridge (GB); Gary Stacey, Cambridge (GB)

(73) Assignee: Covidien LP, Mansfield, MA (US)

( * ) Notice: Subject to any disclaimer, the term of this patent is extended or adjusted under 35 U.S.C. 154(b) by 134 days.

(21) Appl. No.: 16/239,951

(22) Filed: Jan. 4, 2019

(65) Prior Publication Data
US 2019/0133580 A1    May 9, 2019

Related U.S. Application Data

(63) Continuation of application No. 15/150,606, filed on May 10, 2016, now Pat. No. 10,172,615.
(Continued)

(51) Int. Cl.
*A61B 17/072* (2006.01)
*A61B 17/064* (2006.01)
(Continued)

(52) U.S. Cl.
CPC .... *A61B 17/07207* (2013.01); *A61B 17/0644* (2013.01); *A61B 2017/0046* (2013.01);
(Continued)

(58) Field of Classification Search
CPC .......... A61B 17/07207; A61B 17/0644; A61B 2017/07278; A61B 2017/0046;
(Continued)

(56) References Cited

U.S. PATENT DOCUMENTS 3,079,606 A    3/1963  Bobrov et al.
3,490,675 A    1/1970  Green et al.
(Continued)

FOREIGN PATENT DOCUMENTS

AU    198654765      9/1986
CA    2773414 A1    11/2012
(Continued)

OTHER PUBLICATIONS

Japanese Office Action dated Feb. 20, 2020, issued in JP Appln. No. 2016-105078, 7 pages.
(Continued)

*Primary Examiner* — Robert F Long
(74) *Attorney, Agent, or Firm* — Carter, DeLuca & Farrell LLP

(57) ABSTRACT

A surgical stapling device includes a housing and a plurality of cartridges that are coupled together to form a barrel that is rotatably supported within the housing. Each of the cartridges defines a plurality of staple pockets, each supporting a staple. An anvil is coupled to the housing and is movable in relation to the barrel between an open position and a clamped position. A guide shaft extends through the housing and through the barrel. The guide shaft supports a sled and a clamping member. The sled is configured to translate through the barrel to eject the staples from an active cartridge of the plurality of cartridges in response to actuation of a push rod. After firing staples from the active cartridge, the sled and the guide shaft are configured to index or rotate the barrel within the housing to move a second cartridge of the plurality of cartridges to the active position upon retraction and subsequent movement of the sled through a second firing stroke.

19 Claims, 18 Drawing Sheets

Related U.S. Application Data

(60) Provisional application No. 62/166,969, filed on May 27, 2015.

(51) Int. Cl.
  *A61B 17/00* (2006.01)
  *A61B 90/00* (2016.01)
  *A61B 17/29* (2006.01)

(52) U.S. Cl.
  CPC .......... *A61B 2017/00199* (2013.01); *A61B 2017/00398* (2013.01); *A61B 2017/07271* (2013.01); *A61B 2017/07278* (2013.01); *A61B 2017/07285* (2013.01); *A61B 2017/2927* (2013.01); *A61B 2090/034* (2016.02); *A61B 2090/035* (2016.02)

(58) Field of Classification Search
  CPC .. A61B 2017/2927; A61B 2017/00199; A61B 2017/00398; A61B 2017/07271; A61B 2017/07285; A61B 2090/034; A61B 2090/035
  USPC ............................ 227/175.1–182.1; 606/153
  See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,749,114 A * | 6/1988 | Green .............. A61B 17/11 227/19 |
| 4,752,024 A | 6/1988 | Green et al. |
| 4,773,420 A * | 9/1988 | Green .............. A61B 17/11 227/178.1 |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,930,674 A * | 6/1990 | Barak .............. A61B 17/072 227/179.1 |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |

(56) References Cited

U.S. PATENT DOCUMENTS

| | | |
|---|---|---|
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |

(56) References Cited

U.S. PATENT DOCUMENTS

| | | | |
|---|---|---|---|
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |

(56) References Cited

U.S. PATENT DOCUMENTS

| | | |
|---|---|---|
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |

(56) References Cited

U.S. PATENT DOCUMENTS

| | | |
|---|---|---|
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |

(56) References Cited

U.S. PATENT DOCUMENTS

| | | |
|---|---|---|
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,267,849 B2 * | 9/2012 | Wazer ............. A61B 17/07207 600/1 |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Soirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |

(56) References Cited

U.S. PATENT DOCUMENTS

| | | | |
|---|---|---|---|
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,579,785 B2 * | 11/2013 | Shariati ............ A61B 17/07292 600/1 |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,043 B2 * | 12/2013 | Scirica ............ A61B 17/07207 227/175.1 |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 * | 3/2014 | Wazer ................ A61B 17/0644 600/1 |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,851,355 B2 | 10/2014 | Aranyi et al. |
| 9,016,546 B2 | 4/2015 | Demmy et al. |
| 9,027,817 B2 | 5/2015 | Milliman et al. |
| 10,172,615 B2 | 1/2019 | Marczyk et al. |
| 10,349,941 B2 * | 7/2019 | Marczyk ............ A61B 17/0644 |
| 2001/0044656 A1 | 11/2001 | Williamson et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0083808 A1 * | 4/2008 | Scirica ............ A61B 17/07207 227/175.1 |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0197167 A1 * | 8/2008 | Viola ............ A61B 17/07207 227/176.1 |

(56) References Cited

U.S. PATENT DOCUMENTS

| | | |
|---|---|---|
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0302092 A1* | 12/2009 | Kasvikis .......... A61B 17/072 227/180.1 |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0301098 A1* | 12/2010 | Kostrzewski ...... A61B 17/1155 227/179.1 |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0006102 A1* | 1/2011 | Kostrzewski ........ A61B 17/072 227/176.1 |
| 2011/0017801 A1 | 1/2011 | Zemlok et al. |
| 2011/0022032 A1* | 1/2011 | Zemlok ............ A61B 17/07207 606/1 |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0282381 A1 | 11/2011 | Cronin et al. |
| 2011/0282382 A1 | 11/2011 | McAlister et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0001270 A1 | 1/2013 | Kostrzewski |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |

(56) References Cited

U.S. PATENT DOCUMENTS

| | | |
|---|---|---|
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0175316 A1 | 7/2013 | Thompson et al. |
| 2013/0193188 A1 | 8/2013 | Shelton, IV et al. |
| 2013/0277410 A1 | 10/2013 | Fernandez et al. |
| 2013/0334280 A1 | 12/2013 | Krehel et al. |
| 2013/0334281 A1 | 12/2013 | Williams |
| 2014/0001232 A1 | 1/2014 | Cappola et al. |
| 2014/0001233 A1 | 1/2014 | Cappola et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0025046 A1 | 1/2014 | Williams et al. |
| 2014/0027492 A1 | 1/2014 | Williams |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0103092 A1 | 4/2014 | Kostrzewski et al. |
| 2014/0110453 A1 | 4/2014 | Wingardner et al. |
| 2014/0110455 A1 | 4/2014 | Ingmanson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203061 A1 | 7/2014 | Hodgkinson |
| 2014/0203062 A1 | 7/2014 | Viola |
| 2014/0203063 A1 | 7/2014 | Hessler et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239042 A1 | 8/2014 | Simms et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263537 A1 | 9/2014 | Leimbach et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0284372 A1 | 9/2014 | Kostrzewski |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2014/0367448 A1 | 12/2014 | Cappola |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0053749 A1 | 2/2015 | Shelton, IV et al. |
| 2015/0054753 A1 | 2/2015 | Morgan et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |

(56) References Cited

U.S. PATENT DOCUMENTS

| | | | |
|---|---|---|---|
| 2015/0173748 A1 | 6/2015 | Marczyk et al. | |
| 2015/0173749 A1 | 6/2015 | Shelton, IV et al. | |
| 2015/0173750 A1 | 6/2015 | Shelton, IV et al. | |
| 2015/0173755 A1 | 6/2015 | Baxter, III et al. | |
| 2015/0173756 A1 | 6/2015 | Baxter, III et al. | |
| 2015/0173760 A1 | 6/2015 | Shelton, IV et al. | |
| 2015/0173761 A1 | 6/2015 | Shelton, IV et al. | |
| 2015/0173762 A1 | 6/2015 | Shelton, IV et al. | |
| 2016/0345974 A1* | 12/2016 | Marczyk | A61B 17/0644 |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1908414 A2 | 4/2008 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2005160933 A | 6/2005 |
| JP | 2009106752 A | 5/2009 |
| JP | 2014018660 A | 2/2014 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 9622055 A1 | 7/1996 |
| WO | 2004032760 A2 | 4/2004 |
| WO | 2006/081174 A2 | 8/2006 |
| WO | 2009071070 A2 | 6/2009 |

OTHER PUBLICATIONS

Australian Office Action dated Feb. 18, 2020, issued in AU Appln. No. 2016203149, 3 pages.

Extended European Search Report for EP 16 17 1355 dated Oct. 4, 2016.

European Examination Report dated Oct. 6, 2017, issued in EP Application No. 16171355.

* cited by examiner

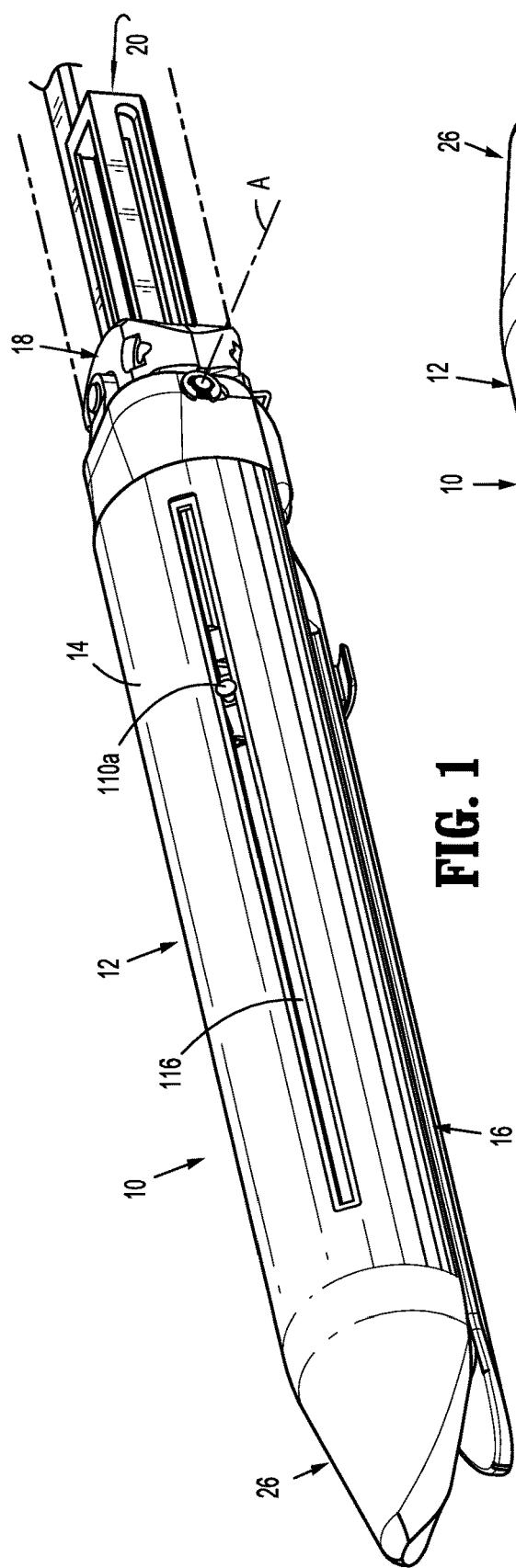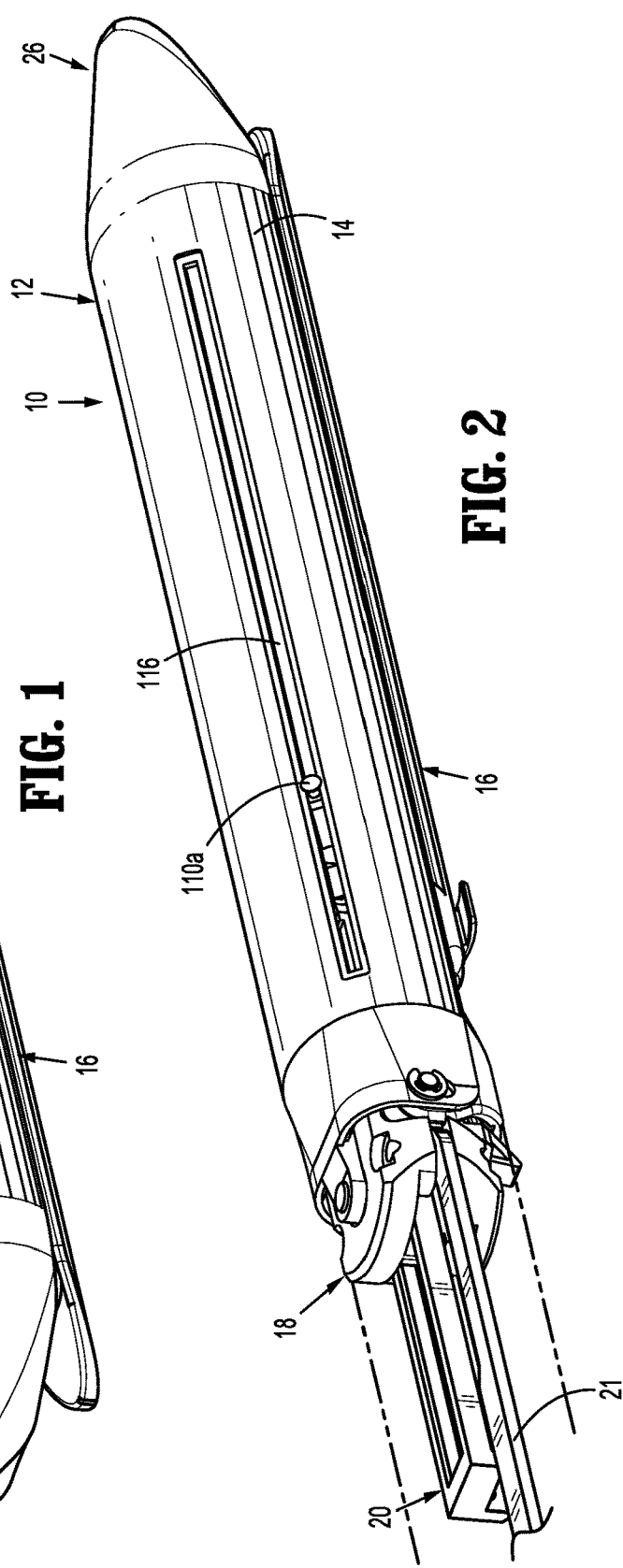

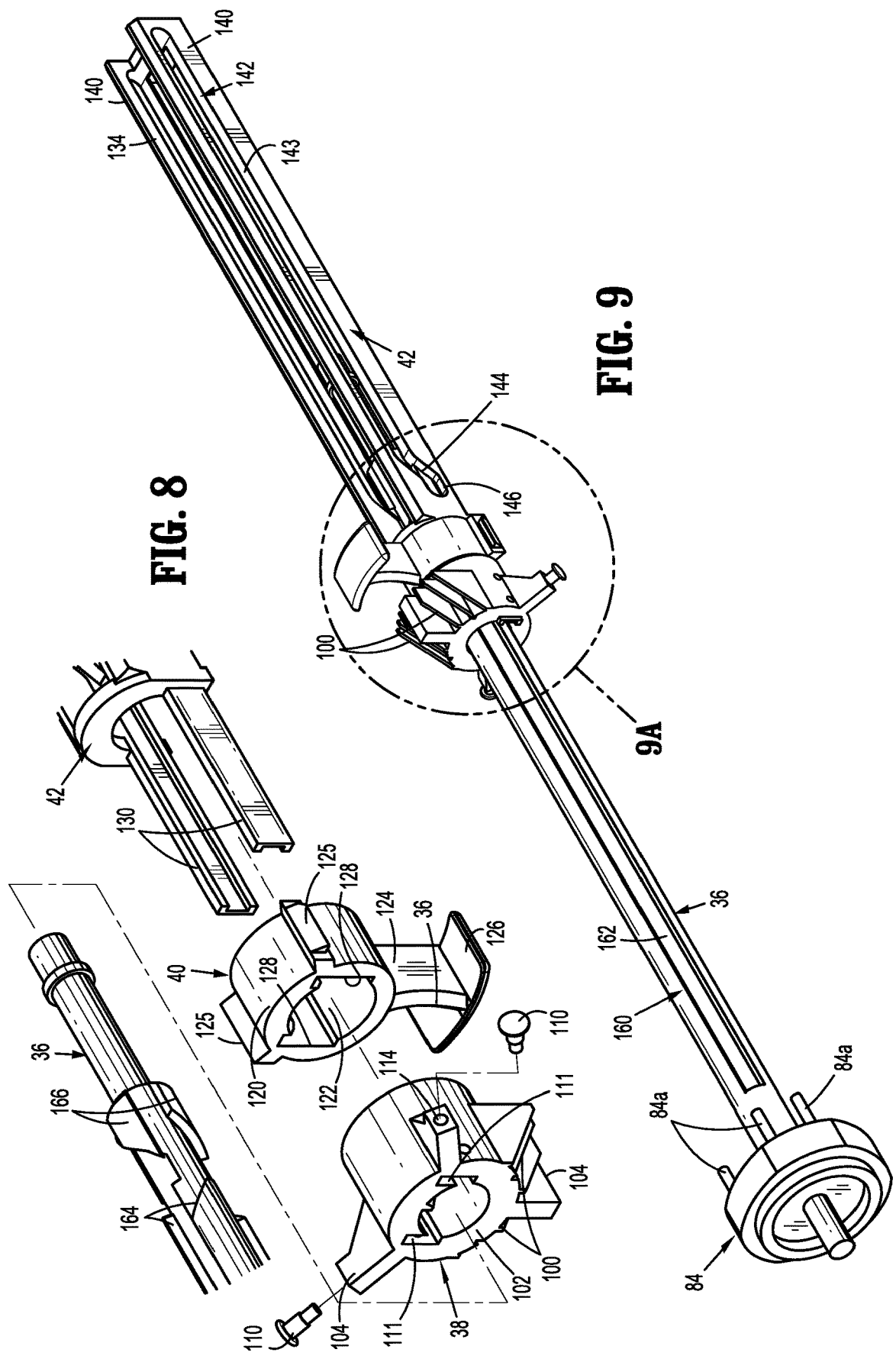

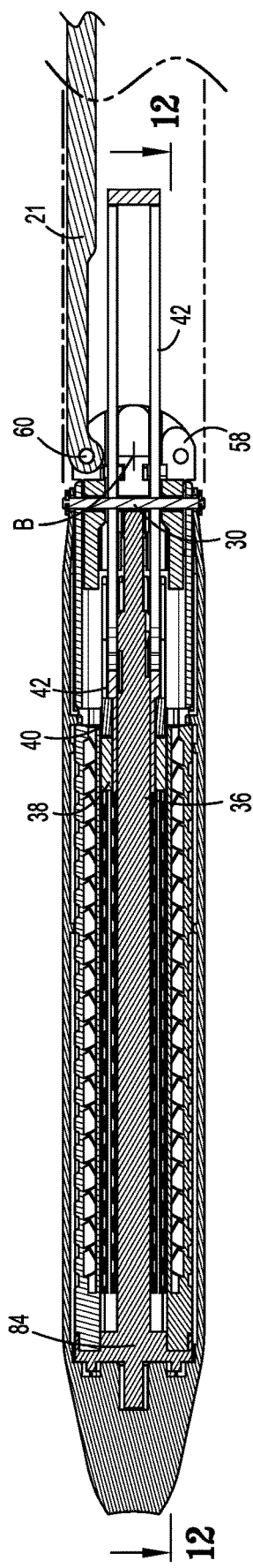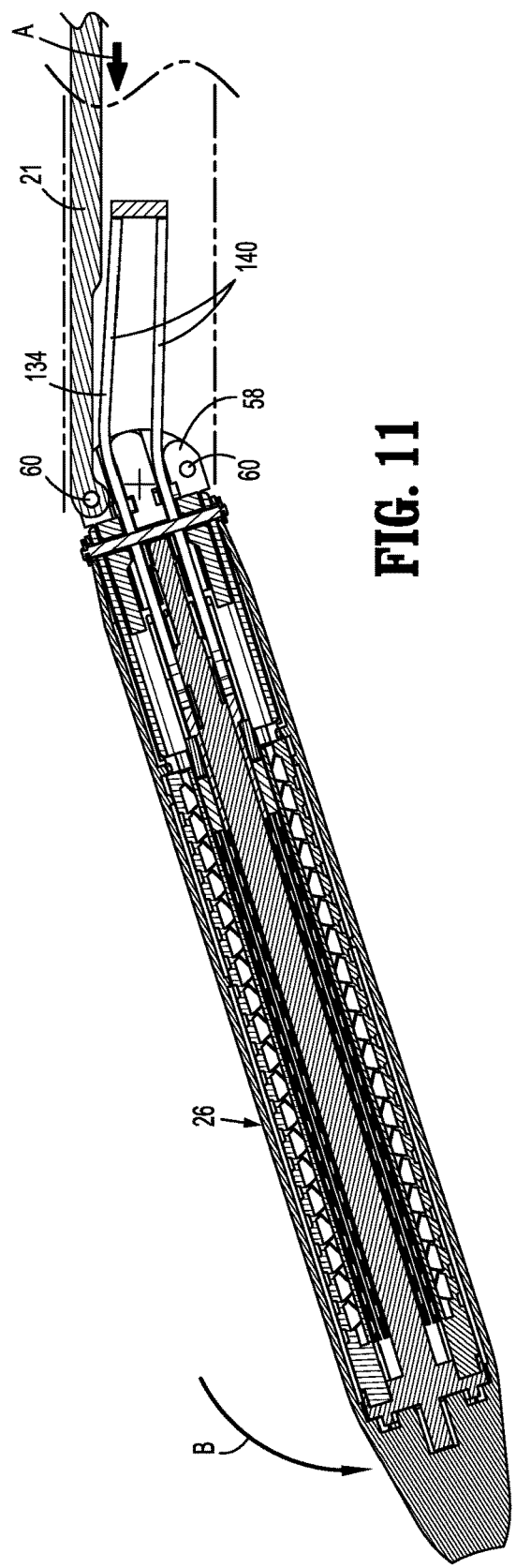

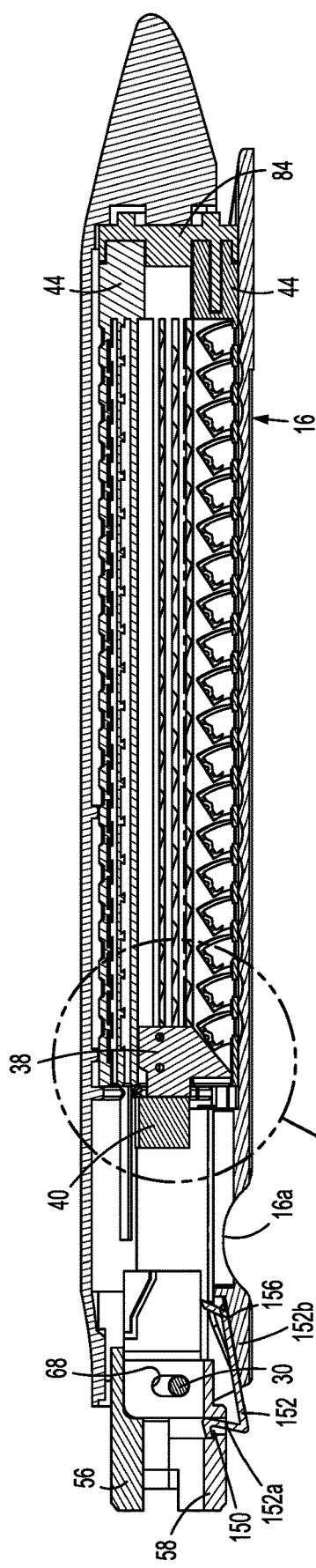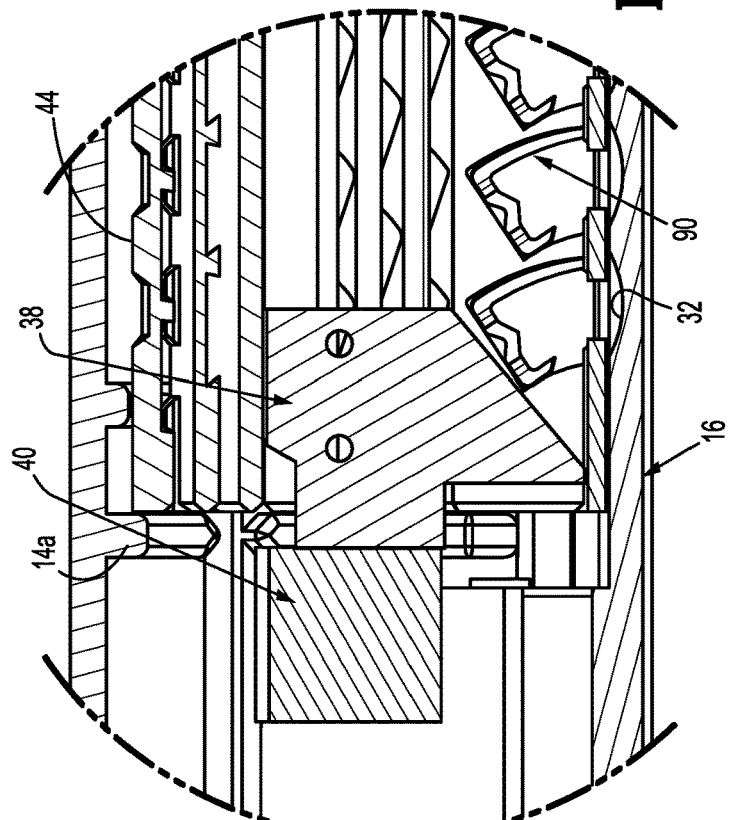

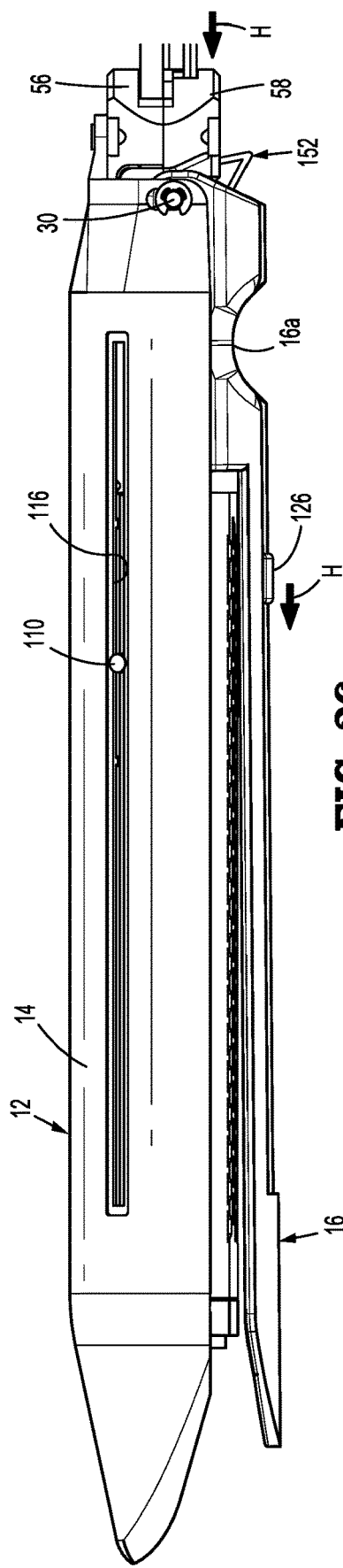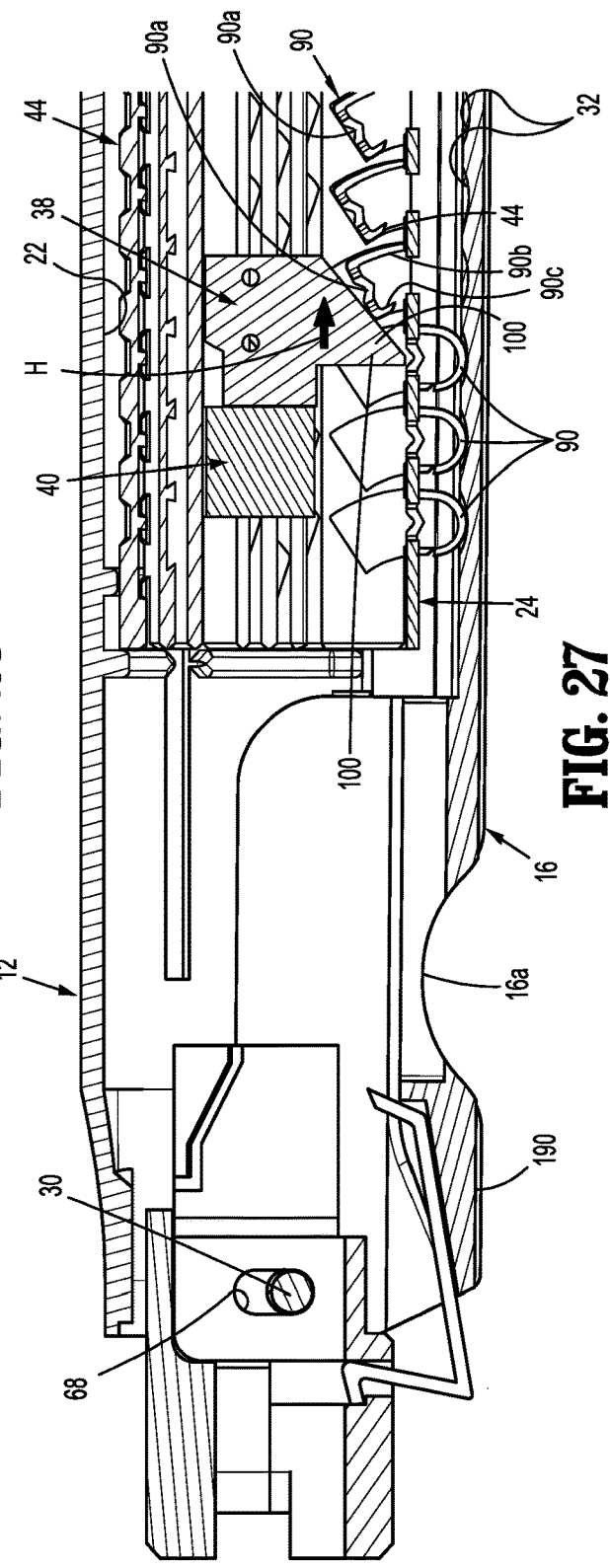

MULTI-FIRE PUSH ROD STAPLING DEVICE

CROSS-REFERENCE TO RELATED APPLICATIONS

This application is a continuation of U.S. application Ser. No. 15/150,606, filed May 10, 2016, which claims the benefit of and priority to U.S. Provisional Patent Application No. 62/166,969 filed May 27, 2015. The entire disclosure of each of which is incorporated by reference herein.

BACKGROUND

Technical Field

The present disclosure relates generally to a surgical stapling device for applying surgical fasteners to body tissue. More particularly, the present disclosure relates to an endoscopic surgical stapling device having a plurality of staple cartridges that are sequentially moved into alignment with an anvil assembly to allow a clinician to fire the stapling device a plurality of times without removing the stapling device from the surgical site.

Background of Related Art

Surgical stapling devices for joining tissue sections are commonly used in surgical procedures. The use of surgical stapling devices as compared to traditional stitching techniques reduces the time required to join and/or cut tissue, thus, reducing the time required to perform a surgical procedure. Reducing the time required to perform a surgical procedure minimizes the time a patient must be anesthetized and, thus minimizes trauma to the patient.

During endoscopic or laparoscopic procedures in which surgery is performed through small incisions or through narrow cannulas inserted through the small incisions in the skin, replacement of the staple cartridge or the loading unit, after firing requires removal of the surgical stapling device from the incision or cannula, replacement of the staple cartridge and/or loading unit and reinsertion of the surgical stapling device into the incision or cannula. This process increases the time required to perform the surgical procedure and increases the likelihood of infection.

It would be advantageous to provide a staple cartridge or loading unit that is capable of being fired a plurality of times before replacement of the staple cartridge or loading unit is required.

SUMMARY

The present disclosure provides in one aspect a surgical stapling device having a housing and a plurality of cartridges coupled together to form a barrel that is rotatably supported within the housing. Each of the cartridges defines a plurality of staple pockets and supports a plurality of staples. An anvil is pivotally coupled to the housing and is movable in relation to the barrel between an open position and a clamped position. Each of the cartridges is sequentially movable into an active position in alignment with the anvil. A guide shaft is rotatably supported within the housing and is rotatably coupled to the barrel such that rotational movement of the guide shaft causes corresponding rotational movement of the barrel. A sled is movably positioned within the housing to translate through the barrel to eject the staples from a first cartridge of the plurality of cartridges in the active position. The sled and the guide shaft are configured such that movement of the sled from a fully retracted position through a firing stroke and a retraction stroke causes the barrel to rotate to move a second cartridge of the plurality of cartridges to the active position.

In some embodiments, the plurality of cartridges includes three cartridges.

In certain embodiments, the guide shaft defines at least one cam channel that includes at least one guide surface and the sled includes a cam member. The cam member is movable into engagement with the at least one guide surface to rotate the barrel to move the second cartridge of the plurality of cartridges to the active position.

In embodiments, the at least one guide surface includes first and second guide surfaces and the cam member is positioned to engage the first guide surface during the firing stroke and to engage the second guide surface during the retraction stroke.

In some embodiments, engagement of the first guide surface of the guide shaft with the cam member of the sled moves the barrel through a first indexing step and engagement of the second guide surface of the guide shaft with the cam member of the sled moves the barrel through a second indexing step, wherein each of the first and second indexing steps rotates the barrel β degrees, wherein β is equal 360 divided by 2x, wherein x is the number of cartridges of the plurality of cartridges.

In certain embodiments, the plurality of cartridges includes three cartridges and each of the indexing steps rotates the barrel 60 degrees.

In embodiments, a push rod has a distal end operatively connected to the sled such that distal movement of the push rod causes distal movement of the sled.

In some embodiments, a clamping member is operatively connected to the push rod such that distal movement of the push rod causes distal movement of the sled and the clamping member.

In certain embodiments, the sled includes a plurality of pusher fingers and each of the cartridges defines a plurality of slots that communicate with the plurality of staple pockets. The plurality of pusher fingers are positioned to translate through the plurality of slots of the cartridge positioned in the active position to eject the plurality of staples from the cartridge in the active position.

In embodiments, the clamping member includes a hub positioned about the guide shaft, a vertical strut extending radially outwardly of the hub and a beam supported on an end of the vertical strut and extending transversely of the vertical strut. Each of the cartridges of the plurality of cartridges and the anvil define a knife slot. The vertical strut is positioned to extend through the knife slots of the cartridge in the active position and of the anvil to position the beam in engagement with an outer surface of the anvil such that distal movement of the clamping member within the cartridge assembly causes the anvil to move from the open position to the clamped position.

In some embodiments, the sled and the clamping member define longitudinal channels and the push rod includes distally extending rails, wherein the distally extending rails are received within the longitudinal channels of the sled and the clamping member to secure the push rod to the sled and the clamping member.

In certain embodiments, the longitudinal channels of the clamping member have a height that is greater than the height of the rails of the push rod such that the clamping member is movable about the guide shaft to move the beam of the clamping member in relation to the cartridge assembly.

In embodiments, a mounting member is secured to the proximal end of the housing and to a proximal end of the anvil by a pivot pin.

In embodiments, the mounting member defines an elongated slot that receives the pivot pin and the cartridge housing defines an elongated through bore that receives the pivot pin. The pivot pin is movable within the elongated slot of the mounting member and the elongated through bore of the cartridge housing to facilitate movement of the pivot pin and the proximal end of the anvil in relation to the proximal end of the mounting member and the proximal end of the cartridge housing.

In embodiments, the activation device includes a handle and an adaptor supported on a distal end of the handle and the surgical stapling device is supported on a distal end of the adaptor.

The present disclosure provides in another aspect a surgical stapling instrument including an activation device and a surgical stapling device. The surgical stapling device has a housing and a plurality of cartridges coupled together to form a barrel that is rotatably supported within the housing. Each of the cartridges defines a plurality of staple pockets and supports a plurality of staples. An anvil is pivotally coupled to the housing and is movable in relation to the barrel between an open position and a clamped position. Each of the cartridges is sequentially movable into an active position in alignment with the anvil. A guide shaft is rotatably supported within the housing and is rotatably coupled to the barrel such that rotational movement of the guide shaft causes corresponding rotational movement of the barrel. A sled is movably positioned within the housing to translate through the barrel to eject the staples from a first cartridge of the plurality of cartridges in the active position. The sled and the guide shaft are configured such that movement of the sled through at least one of a firing stroke and a retraction stroke causes the barrel to rotate to move a second cartridge of the plurality of cartridges to the active position.

In embodiments, the handle is electrically powered.

In some embodiments, each of the cartridges of the plurality of cartridges has a chip including an integrated circuit and the handle includes a processor which can read the chip of each of the cartridges of the plurality of cartridges to identify whether each cartridge of the plurality of cartridges has been fired.

In certain embodiments, the handle includes an LED screen for indicating the current status of the surgical stapling device.

BRIEF DESCRIPTION OF THE DRAWINGS

Various embodiments of the presently disclosed surgical stapling device are described herein with reference to the drawings, wherein:

FIG. 1 is a side perspective view from the distal end of one embodiment of the presently disclosed surgical stapling device with the anvil assembly in a clamped position;

FIG. 2 is a side perspective view from the proximal end of the surgical stapling device shown in FIG. 1;

FIG. 8 is a side, perspective, exploded view of the internal components of the surgical stapling device shown in FIG. 1 including the guide shaft, the sled, the clamping member, and the distal end of the push rod;

FIG. 9 is a side perspective view of the surgical stapling device shown in FIG. 1 with the housing, barrel and mounting assembly removed;

FIG. 10 is a cross-sectional view taken along the longitudinal axis of the surgical stapling device shown in FIG. 1 with the push rod in a retracted position;

FIG. 11 is a cross-sectional view taken along the longitudinal axis of the surgical stapling device shown in FIG. 1 with the push rod in a retracted position and the surgical stapling device articulated;

FIG. 12 is a cross-sectional view taken along section line 12-12 of FIG. 10;

FIG. 13 is an enlarged view of the indicated area of detail shown in FIG. 12;

FIG. 26 is a side view of the surgical stapling device shown in FIG. 1 as the surgical stapling device is being fired;

FIG. 27 is a side cross-sectional view of the proximal end of the surgical stapling device shown in FIG. 1 as the surgical stapling device is being fired;

DETAILED DESCRIPTION OF EMBODIMENTS

Figure 3:
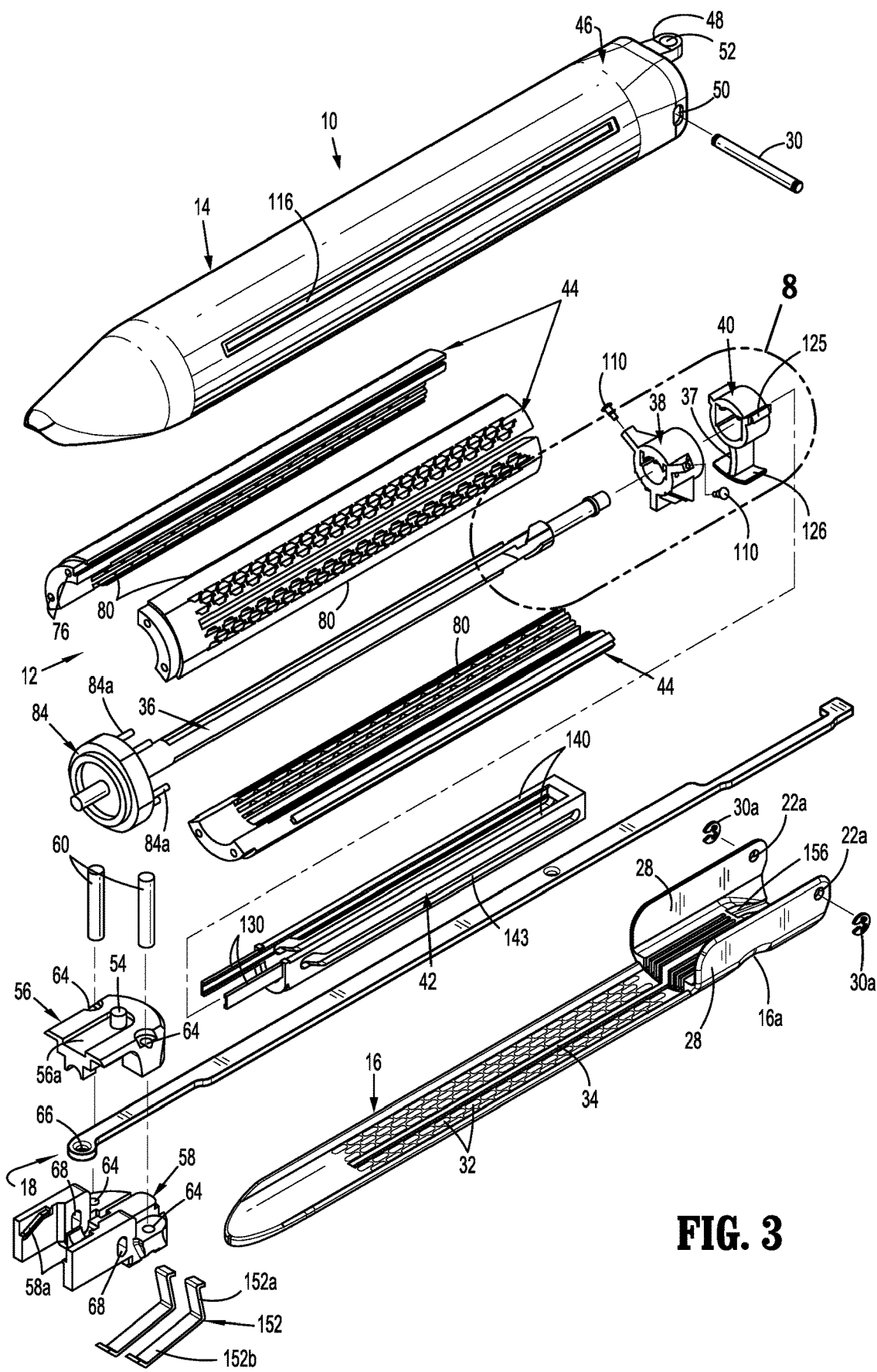
FIG. 3 is an exploded perspective view of the surgical stapling device shown in FIG. 1.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, the term "endoscopic procedures" as used herein refers to any procedure performed through a small incision in the skin or through one or more cannulas and encompasses laparoscopic procedures, arthroscopic procedures, etc.

As described in detail below, the presently disclosed surgical stapling device includes a barrel, formed by a plurality of cartridges connected to each other, that is rotatably supported within a cartridge housing or channel. Each cartridge supports an array of staples and is movable within the cartridge housing to an active position in alignment with an anvil. A sled and a clamping member are supported on a guide shaft for movement through the barrel to engage staples supported within the cartridge in the active position, i.e., the active cartridge, to eject the staples from the cartridge. The guide shaft and the sled are configured to index or rotate the barrel after each use of the surgical stapling device to position a fresh cartridge in the active position to facilitate refiring of the stapling device.

FIGS. 1 and 2 illustrate one embodiment of the presently disclosed surgical stapling device shown generally as 10. The surgical stapling device 10 includes a cartridge assembly 12 including a channel or housing 14, an anvil 16 pivotally secured to the housing 14 about a first axis "A", a mounting assembly 18, a push rod 20 and an articulation rod 21. The housing 14 defines a chamber 22 (FIG. 27) that is dimensioned to rotatably receive a cylindrical barrel 24 (FIG. 14) described in detail below. The anvil 16 and the cartridge assembly 12 define a tool assembly 26 that is pivotally coupled to the mounting assembly 18.

Referring to FIG. 3, the anvil 16 has a proximal end having an outer surface defining a concavity 16a and a pair of spaced flanges 28. Each of the spaced flanges 28 defines an opening 22a that receives a pivot pin 30 to pivotally secure the anvil 16 to the housing 14 of the cartridge assembly 12. The concavity 16a is configured to receive a beam 126 of a clamping member 40 to facilitate movement of the tool assembly 26 to an open position as described in detail below. The anvil 14 defines a plurality of staple deforming recesses 32, and a knife slot 34 that is positioned to receive a knife 37 as described in detail below.

Figure 14:
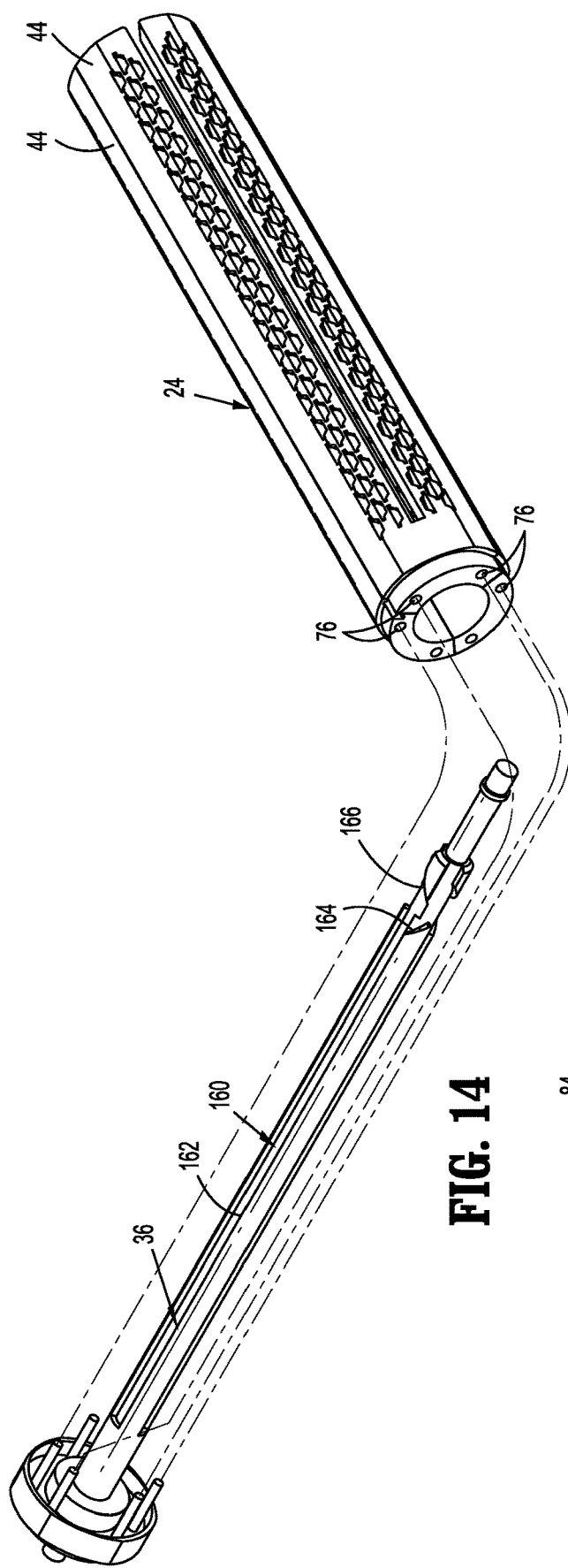
FIG. 14 is a side perspective exploded view of the guide shaft and barrel of the surgical stapling device.
Figure 15:
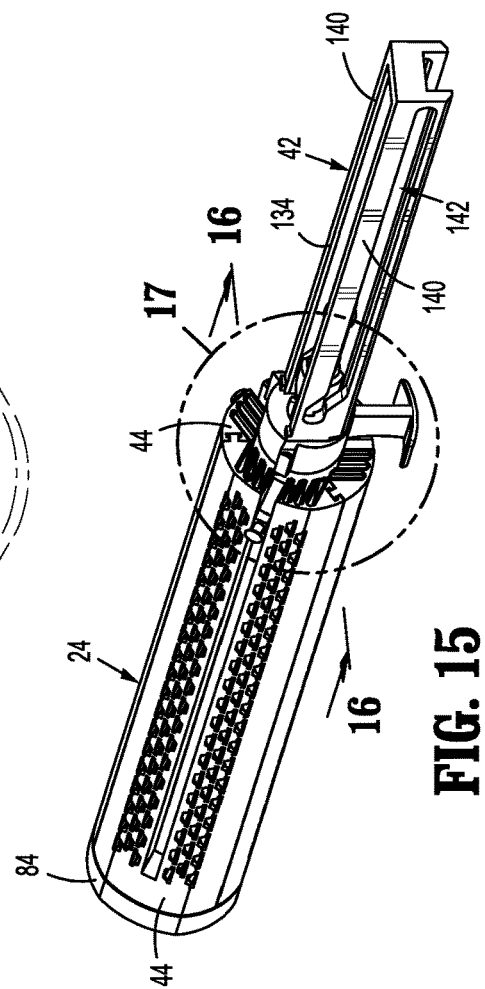
FIG. 15 is a side perspective view of the surgical stapling device shown in FIG. 1 with the housing removed and the push rod.
Figure 16:
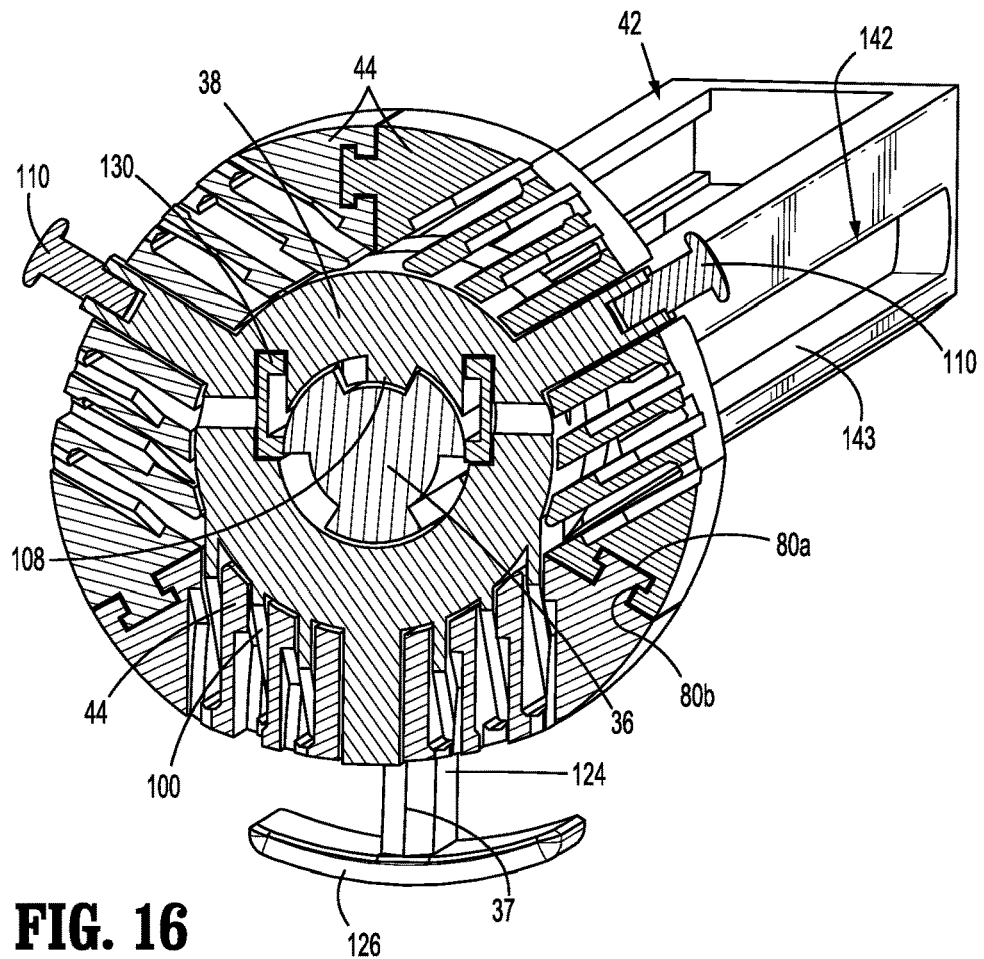
FIG. 16 is a cross-sectional view taken along section line 16-16 of FIG. 15.
Figure 17:
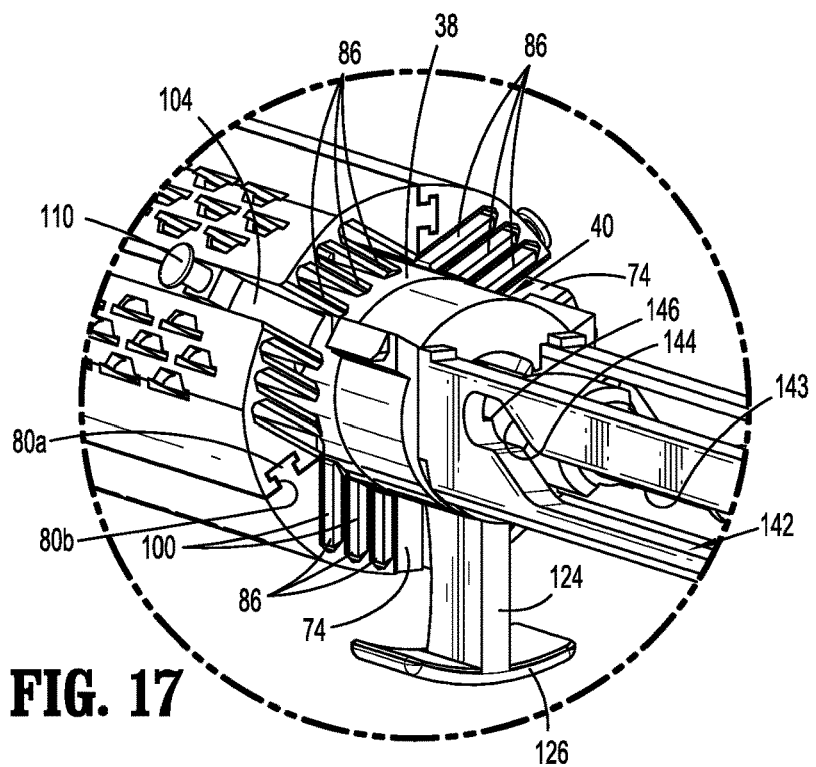
FIG. 17 is an enlarged view of the indicated area of detail shown in FIG. 15.

The cartridge assembly 12 includes a guide shaft 36, a sled 38 and the clamping member 40 which are movably supported about the guide shaft 36, a push rod 42 and a plurality of cartridges 44 that are connected together to define the cylindrical barrel 24 (FIG. 14). Although three cartridges 44 are shown, it is envisioned that the barrel 24 can be formed from two or more cartridges 44, e.g., 2, 4, 5, etc. The cartridge housing 14 has a proximal end 46 that defines a bracket 48 and a transverse through bore 50 that receives the pivot pin 30 to secure the anvil 16 to the cartridge housing 14. Lock washers 30a are provided on each end of the pivot pin 30 to secure the pivot pin to the housing 14 within the through bore 50. The through bore 50 is elongated such that the pivot pin 30 can move within the through bore 50 to allow the proximal end of the anvil 16 to move toward and away from the barrel 24 of the cartridge assembly 12 as described below. The bracket 48 defines an opening 52 that receives a pin 54 formed on an upper member 56 of the mounting assembly 18 to secure the cartridge assembly 12 to the mounting assembly 18. The bracket 48 is received in a recess 56a in the upper member 56 to fixedly secure the cartridge housing 14 to the mounting assembly 18.

The mounting assembly 18 includes the upper member 56 and a lower member 58. As discussed above, the upper member 56 is secured to the bracket 48 of the cartridge housing 14 by the pin 54. The lower member 58 of the mounting assembly 18 is secured to the upper member 56 by a pair of pins 60. More specifically, each of the upper and lower members 56 and 58 defines openings 64 that receive the pins 60 to secure the upper and lower members 56 and 58 together. One of the pins 60 is positioned through an opening 66 in a distal end of the articulation rod 21 to secure the articulation rod 21 to the mounting assembly 18. As described below in further detail, linear movement of the articulation rod 21 pivots the mounting assembly 18 and the tool assembly 26 about an axis transverse to axis "A" (FIG. 1) The lower member 58 of the mounting assembly 18 defines two spaced elongated slots 68 that receive the pivot pin 30. The elongated slots 68 allow the pivot pin 30 to move within the slots 68 to allow the proximal end of the anvil 16 to move toward and away from the proximal end of the cartridge assembly 12 as described below.

Figure 4:
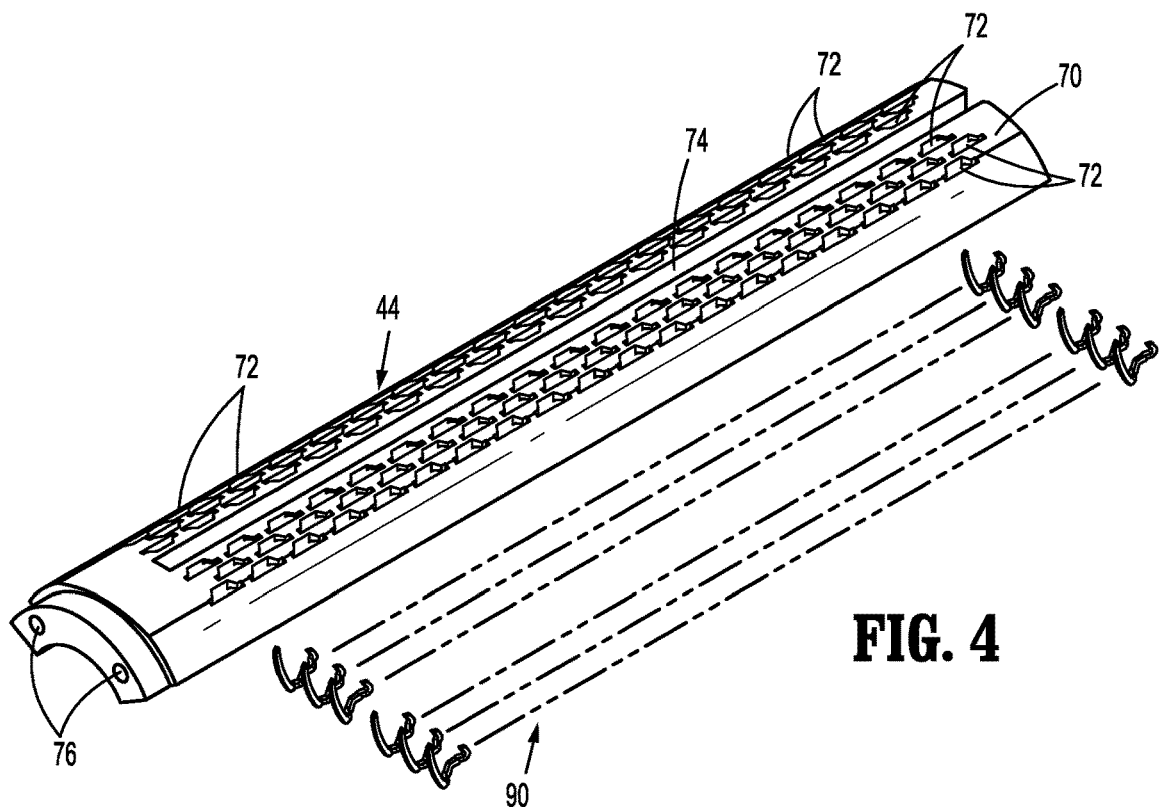
FIG. 4 is a side exploded, perspective view of one of the cartridges of the surgical stapling device shown in FIG. 1.
Figure 5:
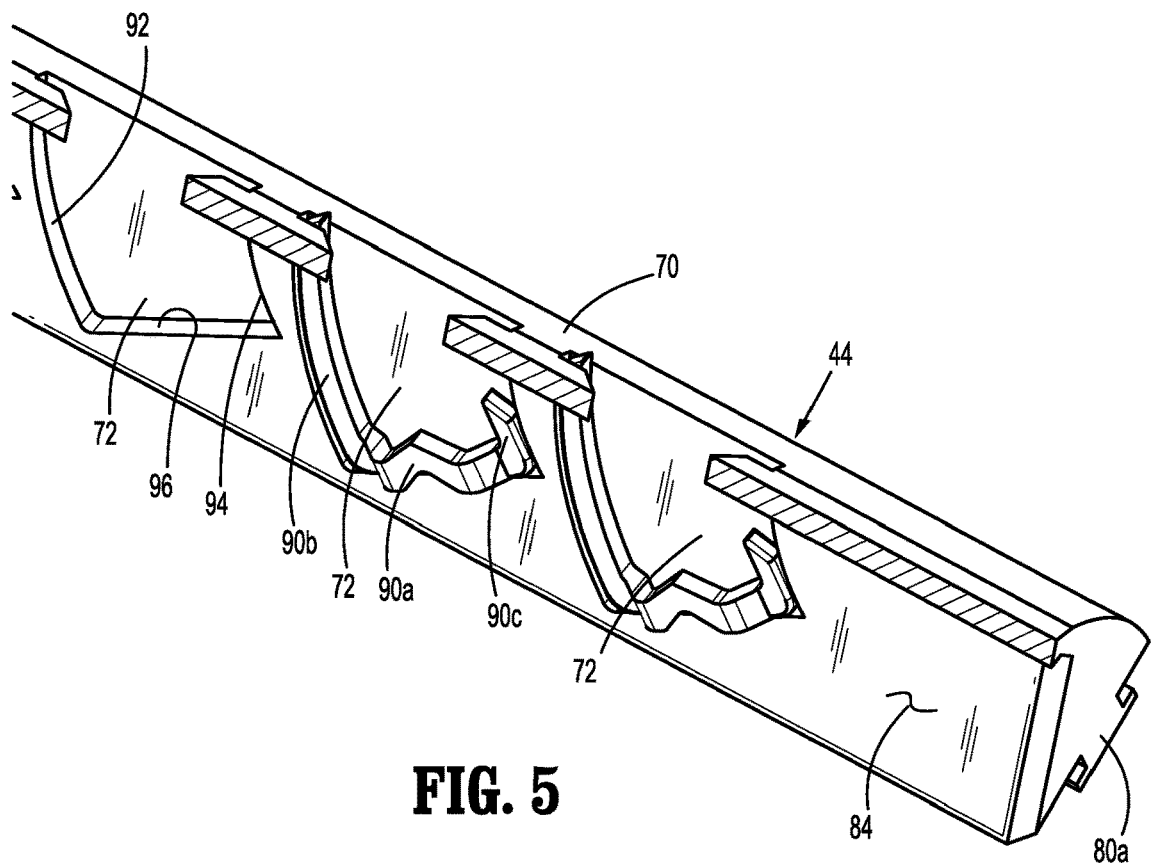
FIG. 5 is a side cross-sectional view through a portion of the cartridge shown in FIG. 4 with the staples positioned in the staple pockets of the cartridge.

Referring to FIGS. 4 and 5, each cartridge 44 includes a cartridge body 70 defining a plurality of rows of staple pockets 72 and a knife slot 74. Each staple pocket 72 supports a staple as described in detail below. In embodiments, the body 70 defines three linear rows of staple pockets 72 on each side of the knife slot 74. Alternately, the body 70 may define one or more rows of staple pockets 72 on each side of the knife slot 74. Each cartridge body 70 has a distal end defining two spaced blind bores 76, and a coupling member 80 positioned on each of the side edges of the cartridge body 70. In embodiments, the coupling member 80 includes a dove-tail projection 80a positioned along one side edge of the cartridge body 70 and a dove-tail groove 80b positioned along an opposite side edge of the cartridge body 70 (FIG. 9B). The dove-tail projections 80a and grooves 80b facilitate attachment of each cartridge 44 to adjacent cartridges 44 to define the cylindrical barrel 24 (FIG. 9B). The blind bores 76 at the distal end of each cartridge 44 receive the legs 84a of an end cap 84 of the guide shaft 36 to secure the cartridges 26 in a radially and axially fixed position in relation to each other and to rotatably fix the guide shaft 36 to the barrel 24. The end cap 84 is fixedly secured to the distal end of the guide shaft 36 such that rotation of the guide shaft 36 causes rotation of the barrel 24. In addition, the end cap 84 is rotatably supported in the distal end of the housing 14 of the cartridge assembly 12 to rotatably support the guide shaft 36 within the housing 14. The inner surface of the housing 14 of the cartridge assembly 12 includes an annular flange 14a (FIG. 13) that retains the barrel 24 in a distal end of the housing 14.

Each cartridge body 70 defines a plurality of slots 86 (FIG. 9B), wherein each slot 86 is aligned with a row of staples 90. In the illustrated embodiment, each cartridge body 70 defines three rows of staples 90 on each side of the knife slot 74 and, thus, defines three slots 86 on each side of the knife slot 74.

Figure 6:
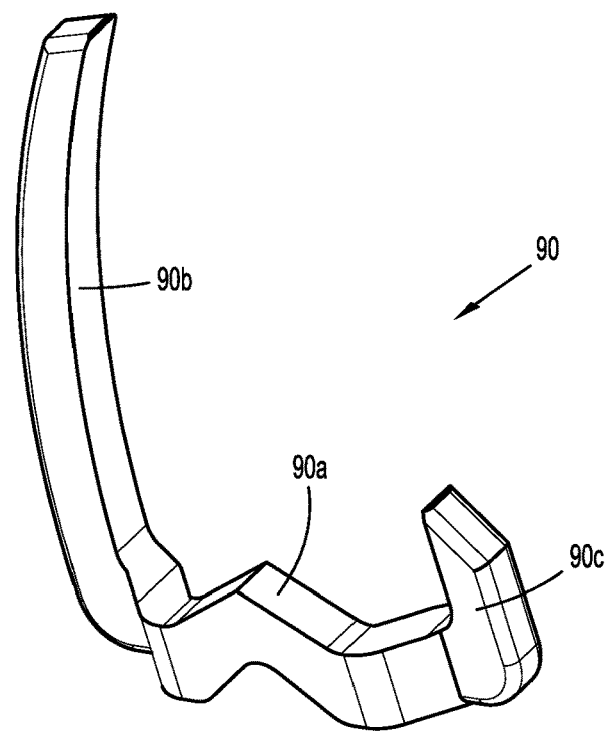
FIG. 6 is a side perspective view of one of the staples of the cartridges shown in FIG. 5.
Figure 7:
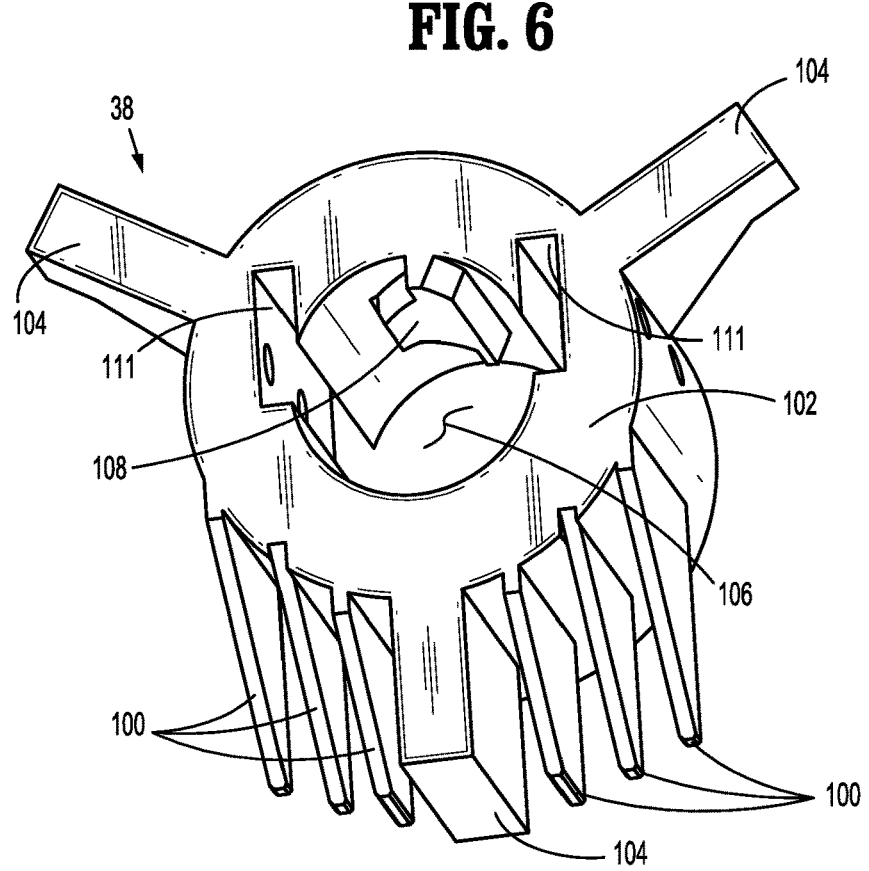
FIG. 7 is a perspective view from the distal end of the sled of the surgical stapling device shown in FIG. 1.

Referring also to FIG. 6, each staple pocket 72 has a curved distal wall 92, a curved proximal wall 94 and angled shelf 96 that extends between the distal and proximal walls 92, 94. Each of the staples 90 includes the backspan 90a, a first leg 90b and a second leg 90c. The shelf 96 supports the backspan 90a of the staple 90. The first leg 90b extends from one end of the backspan 90a and is elongated and curved. When a staple 90 is supported in the staple pocket 72, the first leg 90b is positioned adjacent to the curved distal wall 92 of a respective staple pocket 72. The second leg 90c has a length that is substantially shorter than the length of the first leg 90b and is positioned adjacent the proximal wall 94 of the staple pocket 72. In embodiments, the first leg 90b has a length between 2 and 10 times greater than the length of the second leg 90c. In certain embodiments, the first leg 90b has a length between 4 and 8 times greater than the length of the second leg 90c. The backspan 90a of each staple 90 has a triangular or V-shaped configuration and includes a central portion that is offset from a common plane defined by the first and second legs 90b, 90c of the staple 90. As such, the backspan 90a extends outwardly of the shelf 96 of the staple pocket 72 and into a respective slot 86 defined by the cartridge body 70 such that movement of pusher fingers 100 of the sled 38 through the slots 86 of the cartridge body 70 causes the staples 90 to be ejected from the staple pockets 72 as described in detail below.

The presently disclosed staple geometry facilitates deformation of the staple 90 from a non-deformed configuration to a deformed or closed configuration (FIG. 27) by deforming only the first, elongated leg 90b towards the shorter leg 90c. This eliminates the need for pushers that engage the backspan of staples, as are conventional in the prior art, to deform the staples 90. It is envisioned that the second leg 90c may be completely removed from the staple 90.

Figure 9A:
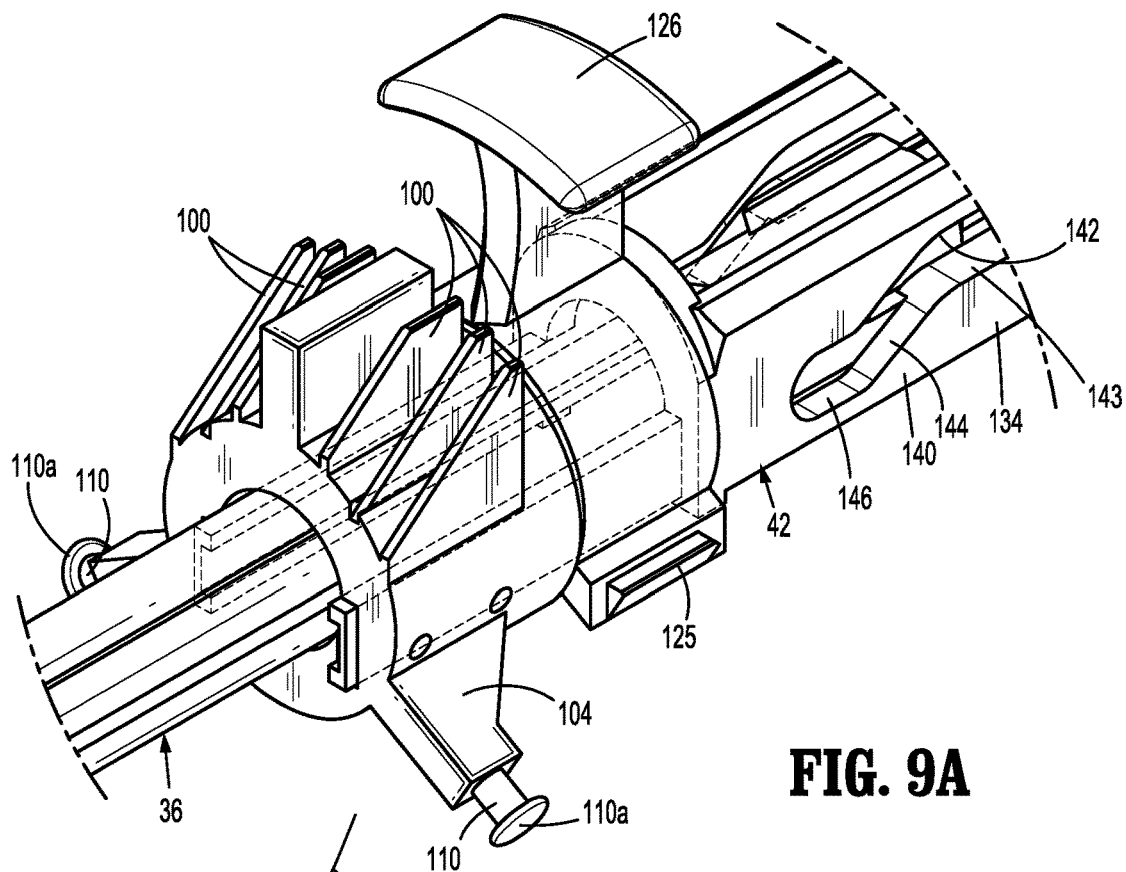
FIG. 9A is an enlarged view of the indicated area of detail shown in FIG. 9.
Figure 9B:
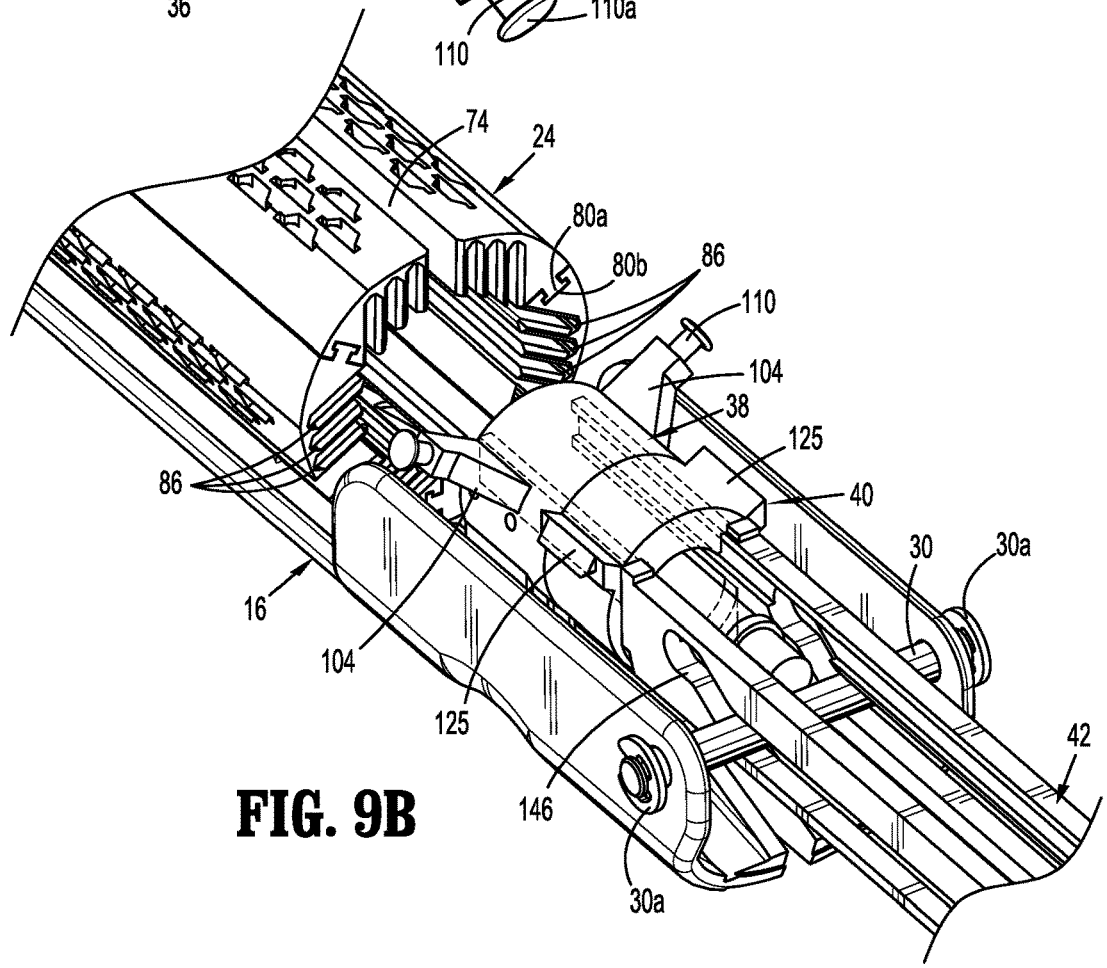
FIG. 9B is an enlarged view of the proximal end of the surgical stapling device shown in FIG. 1 with the housing removed.

Referring to FIGS. 7-9B, the sled 38 includes a hub 102, a plurality of fins 104, and the plurality of pusher fingers 100. The hub 102 defines a longitudinal bore 106 that receives the guide shaft 36 (FIG. 9). A cam member 108 is formed on an inner wall of the hub 102 within the longitudinal bore 106. The cam member 108 is configured to operatively engage the guide shaft 36 to effect indexing of the barrel 24 as described in detail below.

The plurality of pusher fingers 100 and the fins 104 of the sled 38 extend radially outwardly from the hub 102. Each of the plurality of fingers 100 is received within and is translatable through a respective slot 86 defined within the cartridge body 70 and is translatable through the slot 86 (FIG. 9B) in response to movement of the sled 38 about the guide shaft 36 to eject a row of the staples 90 (FIG. 4) from the cartridge body 70. Each of the fins 104 is positioned to translate through the knife slot 74 of a respective one of the cartridges 44 to prevent rotation of the barrel 24 in relation to the sled 38 as the tool assembly 26 is being fired. When the sled 38 is in a retracted position, the fins 104 are spaced proximally of the knife slots 74 such that the barrel 24 is rotatable in relation to the sled 38.

Each of the fins 104 supports a retainer 110 on its outer periphery. In embodiments, each retainer 110 includes a screw or rivet that is received within a bore 114 (FIG. 8) defined in an outer surface of one of the fins 104. The retainers 110 extend through elongated slots 116 (FIG. 1) in the cartridge housing 14 to prevent the sled 38 from rotating in relation to the cartridge housing 14. Each of the retainers 110 may include an enlarged head 110a that has a width that is greater than the width of the slots 116 to prevent the retainer 110 from being disengaged from the housing 14.

In embodiments, the sled 38 also defines a pair of longitudinal channels 111 that extend from a proximal end of the sled 38 at least partially through the sled 38. The channels 111 are provided to facilitate securement of the sled 38 to the push rod 42 as described in detail below.

The clamping member 40 includes a hub 120 defining a longitudinal bore 122, and a vertical strut 124 and protrusions 125 that extend radially outward from the hub 120. A beam 126 is supported on the outer end of the vertical strut 124. The vertical strut 124 is dimensioned to extend through the knife slot 74 (FIG. 4) of an active cartridge 44 of the plurality of cartridges 44. As used herein, the term "active cartridge" refers to the cartridge 44 of the plurality of cartridges 44 that is currently aligned with the anvil 16. The beam 126 is supported on the vertical strut 124 to engage an outer surface of the anvil 16 as the clamp member 40 is moved distally through the cartridge assembly 12 to move the anvil 16 from an open position to a clamped position in relation to the cartridge assembly 12 and to define a maximum tissue gap between the cartridge assembly 14 and anvil 16 during firing.

The protrusions 125 of the clamping member 40 are positioned to engage ledges 58a (FIG. 3) formed on the inner walls of the lower mounting member 58 (FIG. 3) of the mounting assembly 18 when the clamping member 40 is in a fully retracted position. Engagement of the protrusions 125 with the ledges 58a moves the beam 126 of the clamping member 40 towards the cartridge assembly 12 to move the anvil 16 towards the cartridge assembly 12 and position the anvil 16 and the cartridge assembly 12 in a parked or closely approximated position as described below.

The clamping member 40 also defines longitudinal channels 128 that are aligned with the longitudinal channels 111 of the sled 38. The longitudinal channels 111 and 128 of the sled 38 and clamping member 40, respectively, receive rails 130 (FIG. 8) that extend from the distal end of the push rod 42 to secure the push rod 42 to the sled 38 and the clamping member 40. In embodiments, the channels 111 of the sled 38 are configured to receive the rails 130 of the push rod 42 to secure the push rod 42 to the sled 38 such that axial movement of the push rod 42 is translated into axial movement of the sled 38. In contrast, the channels 128 of the clamping member 40 have a height that is greater than the height of the rails 130 (FIG. 19A) to allow the clamping member 40 to move upwardly about the rails 130 when the protrusions 125 of the clamping member 40 engage the ledges 58a of the lower mounting member 58 (FIG. 3) to facilitate movement of the tool assembly 26 of the surgical stapling device 10 to a parked position as described in further detail below. Since the clamping member 40 is positioned between the distal end of the push rod 42 and the proximal end of the sled 38, axial movement of the push rod 42 is also translated to axial movement of the clamping member 40. The rails 130 can be secured to the sled 38 using any of a variety of fastening techniques including sonic welding, friction, adhesives, pins, interlocking components, etc. When the push rod 42 is advanced by an actuation device 200 (FIG. 31), the push rod 42 advances the sled 38 and the clamping member 40 along the guide shaft 36 through the barrel 24 as described in detail below.

The push rod 42 has an elongated, flexible body 134 having first and second sidewalls 140 and is movable about the guide shaft 36. Each sidewall 140 defines an elongated cam slot 142 that has a substantially linear portion 143 along a majority of its length but has an angled distal portion 144 and a short distal linear portion 146 positioned distally of the angled distal portion 144. The cam slot 142 receives the pivot pin 30 that pivotally supports the proximal end of the anvil 16. As such, movement of the push rod 42 in relation to the pivot pin 30 moves the pivot pin 30 within the transverse through bore 50 of the cartridge housing 14 to change the position of the proximal end of the anvil 16 in relation to the barrel 24 of the cartridge assembly 12.

Figure 31:
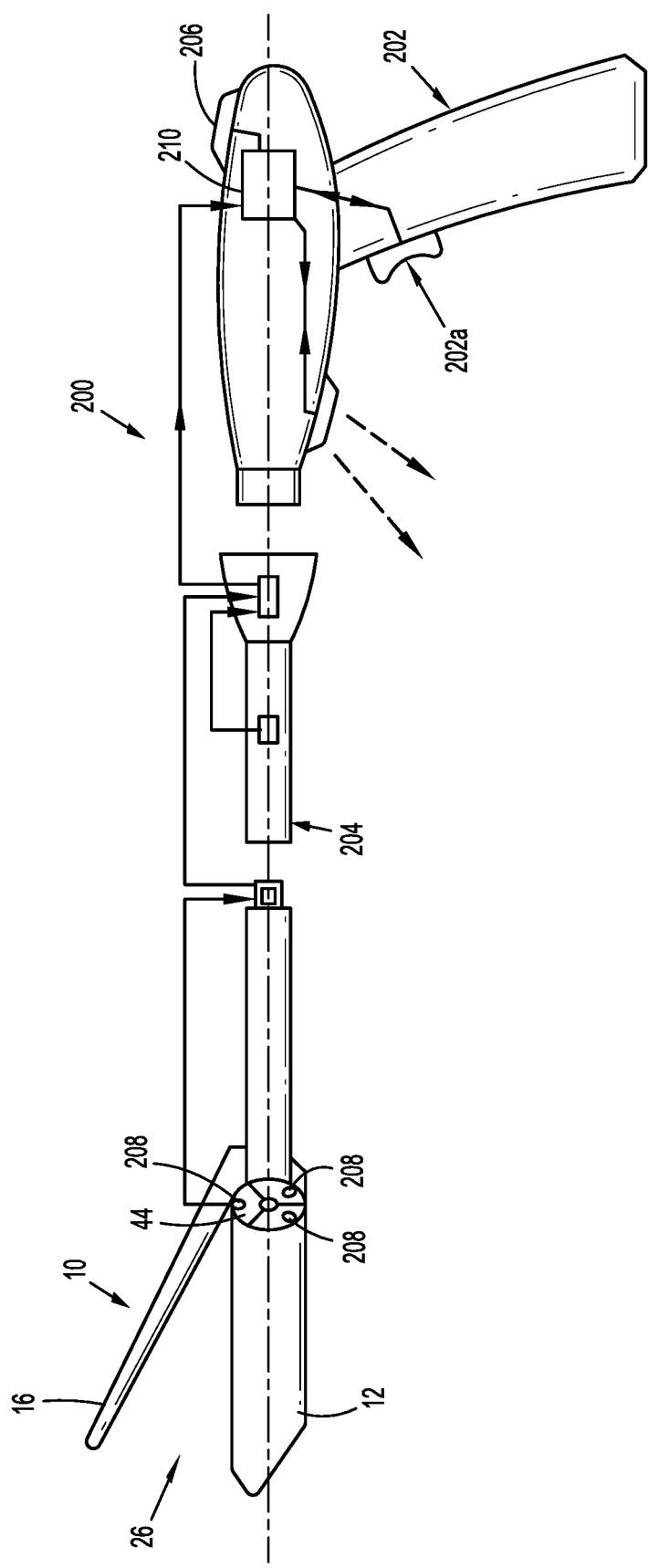
FIG. 31 is a schematic view of an actuation device suitable for use with the surgical stapling device shown in FIG. 1.

Referring to FIGS. 10 and 11, although not shown, the surgical stapling device 10 is intended to be pivotally supported on the distal end of an actuation device 200 shown schematically in FIG. 31 such that the surgical stapling device can be articulated about an articulation axis that is transverse to axis "A" (FIG. 1). In order to articulate the surgical stapling device 10 about the articulation axis, the distal end of the articulation rod 21 is connected to one of the pins 60 that secure the upper and lower mounting members 56 and 58 of the mounting assembly 18 together at a position offset from the articulation axis. When the articulation rod 21 is moved in the direction indicated by arrow "A" in FIG. 11, the tool assembly 26 will pivot in the direction indicated by the arrow "B" in FIG. 11 and vice versa. As illustrated, the sidewalls 140 of the flexible body 134 of the push rod 42 bends about the articulation axis when the surgical stapling device 10 is fired with the tool assembly 26 in an articulated position.

Referring to FIGS. 12 and 13, the lower mounting member 58 defines openings 150. Each opening 150 receives a proximal end of a biasing member, e.g., a leaf spring 152. Each leaf spring 152 includes a bent portion 152a and an elongated portion 152b. The bent portion 152a is securely fitted into the opening 150 of the lower mounting member 58 and the elongated portion 152b is positioned to engage a ramped surface 156 at the proximal end of the anvil 16 to urge the anvil 16 towards the open position.

Referring to FIGS. 14-17, the guide shaft 36 defines a plurality of cam channels 160. Each of the cam channels 160 is movable to a position to receive the cam member 108 of the sled 38. Each cam channel 160 has a substantially straight portion 162 that extends the majority of the length of the guide shaft 36, an angled first guide surface 164 and an angled second guide surface 166. When the sled 38 is initially moved along the guide shaft 36 distally from a fully retracted position, the cam member 108 of the sled 38 will engage the first guide surface 164 to urge guide shaft 36 laterally of the sled 38. As discussed above, the sled 38 includes fins 104 that extend through the slots 116 (FIG. 1) of the housing 14 to prevent rotation of the sled 38 within the housing 14. Thus, engagement of the cam member 108 of the sled 38 and the first guide surface 164 of the guide shaft 36 causes rotation of the guide shaft 38 in a half indexing movement as described below. Engagement of the cam member 108 and the first guide surface 164 will occur prior to the fins 104 of the sled 38 entering the barrel 24 and the pusher fingers 100 of the sled 38 entering the slots 86 of the cartridge body 70 of the active cartridge 44 which would prevent rotation of the barrel within the housing 14. As discussed above, the barrel 24 is supported on the on the legs 84a of the end cap 84 which is fixedly secured to the guide shaft 36. As such, when the cam member 108 of the sled 38 engages the first guide surface 164 of the guide shaft 36 and the guide shaft 36 rotates, the barrel 24 will also rotate. The first guide surface 164 is configured to rotate the barrel 60 degrees upon engagement with the cam member 108 of the sled 38. It is envisioned that if the barrel 24 were to include more or less than three cartridges 44, the configuration of the first cam surface 164 and/or the cam member 108 can be changed to achieve the desired degree of rotation of the barrel 24.

After the surgical stapling device 10 is fired and the sled 38 is moved through a retraction stroke towards its retracted position, the cam member 108 will engage the second guide surface 166 to rotate the guide shaft 36 sixty degrees in a half indexing movement as described below. As discussed above, engagement of the cam member 108 and the second guide surface 166 will occur after the fins 104 of the sled 38 exit the knife slots 74 of the barrel 24 and the pusher fingers 100 of the sled 38 exit the slots 86 of the cartridge body 70 of the cartridge 44 that was just fired.

In use, the surgical stapling device 10 is moved from a "parked position" through a first indexing step to an "open position". From the "open position" the surgical stapling device 10 is moved to a "clamped position" and then through a firing stroke. After the surgical stapling device 10 is fired, the surgical stapling device 10 is moved through a retraction stroke wherein the surgical stapling device moves through a second indexing step. In the "parked position", the anvil 16 is held in close alignment with the cartridge assembly 12. During the first indexing step, the barrel 24 is rotated to align a cartridge with the anvil 16 as described in further detail below. In the "open position", the anvil 16 and cartridge assembly 12 are biased open by the leaf springs 152. In the "clamped position", the anvil 16 is moved into close approximation with the cartridge assembly 12. During the firing stroke, the pusher fingers 100 of the sled 38 translate through the active cartridge 44 to engage and eject the staples 90 from the active cartridge 44. During the retraction stroke, the barrel 24 is moved through the second indexing step to rotate a new (unfired) cartridge partially toward the active position as described in detail below. Each of these positions and strokes will be described below.

Figure 18:
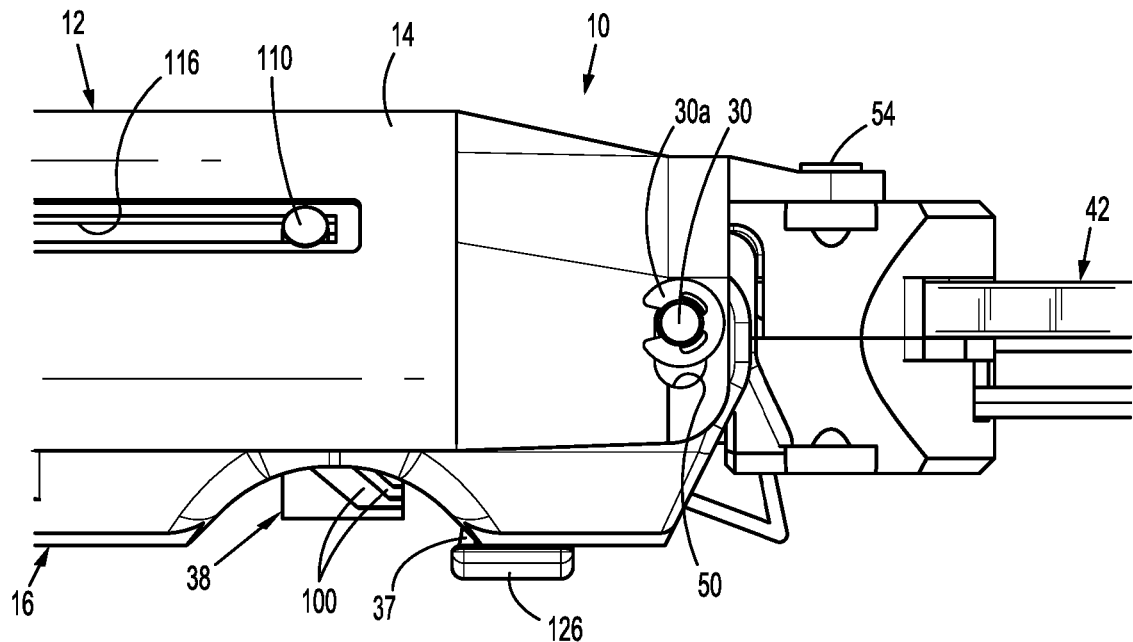
FIG. 18 is a side view of the proximal end of the surgical stapling device shown in FIG. 1 with the surgical stapling device in the parked position.
Figure 19:
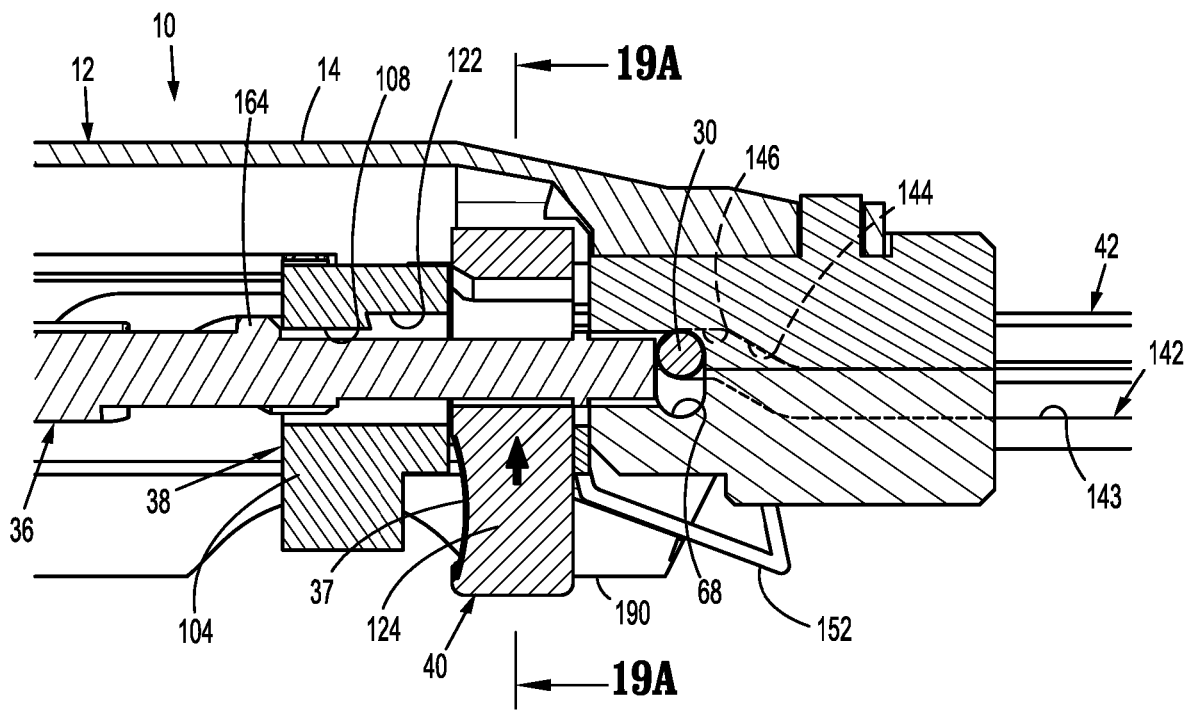
FIG. 19 is a side view of the proximal end of the surgical stapling device shown in FIG. 1 with the housing and barrel removed and the surgical stapling device in the parked position.
Figure 19A:
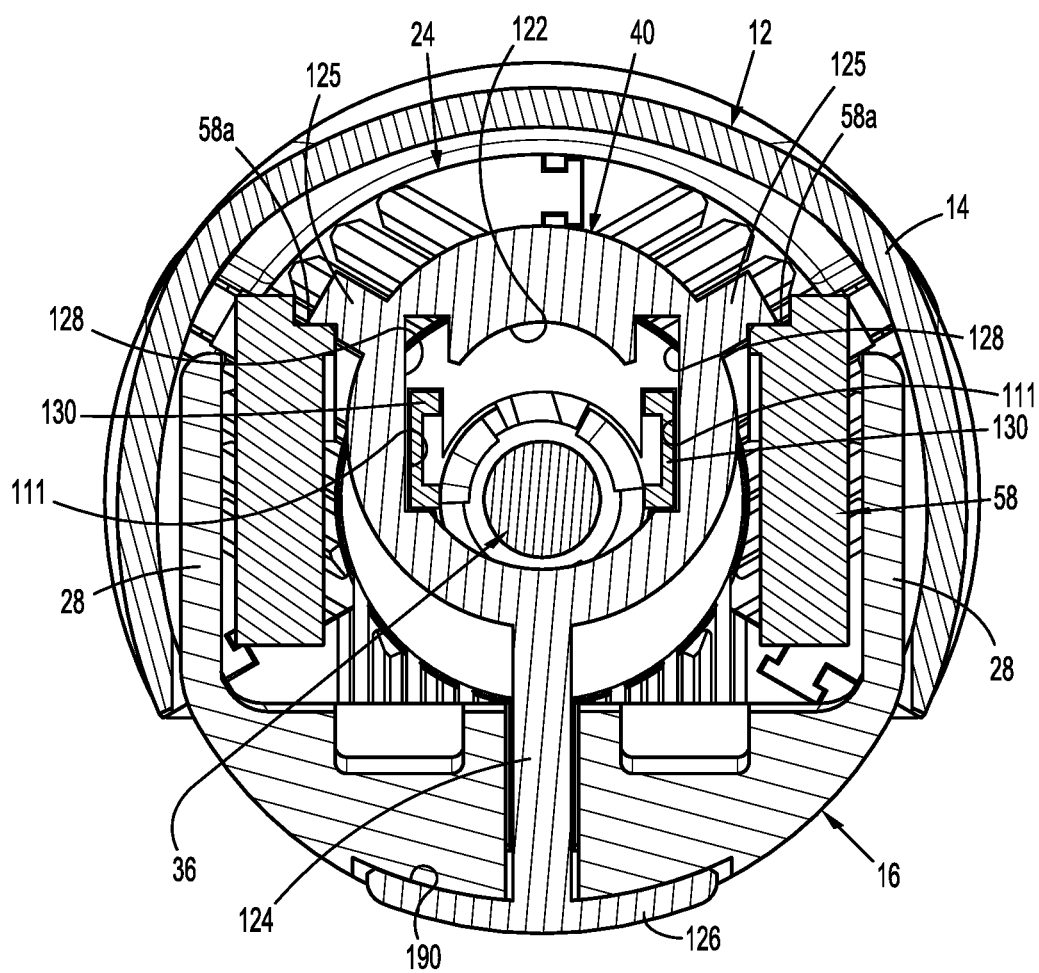
FIG. 19A is a cross-sectional view taken along section line 19A-19A of FIG. 19.

FIGS. 18-19A illustrate a proximal end of the surgical stapling device 10 when the surgical stapling device 10 is in the parked position. In the parked position, the push rod 42 is in its fully retracted position with the pivot pin 30 positioned in the short distal linear portion 146 of the cam slot 142 of the push rod 42. In this position of the push rod 42, the pivot pin 30 is retained in the upper end of the through bore 50 of the cartridge 14 and the upper end of the elongated slot 68 of the mounting assembly 18 to hold the proximal end of the anvil 16 in close approximation with the cartridge assembly 12. When the push rod 42 is in its retracted position, the sled 38 and the clamping member 40 are positioned proximally of the barrel 24 (FIG. 21) and the protrusions 125 (FIG. 19A) of the clamping member 40 are engaged with the ledges 58a of the lower mounting member 58 of the mounting assembly 18. When the protrusions 125 are positioned on the ledges 58a of the lower mounting member 58, the beam 126 of the clamping member 40 is raised up into engagement with an outer surface 190 of a proximal end of the anvil 16 to retain the anvil 16 in engagement with the cartridge assembly 12.

In the parked position, the diameter of the stapling device 10 is minimized to facilitate insertion of the stapling device 10 through a small diameter cannula assembly (not shown). In addition, as best shown in FIG. 19, the cam member 108 is positioned slightly proximally of the first guide surface 164 of the guide shaft 36. It is also noted that in the parked position, the anvil is positioned halfway between two adjacent cartridges 44. More specifically, one half of each of two adjacent cartridges 44 is positioned in opposition to the anvil 16. As such, the pusher fingers 100 are not aligned with the cartridge slots 84 of the cartridge bodies 70.

Figure 20:
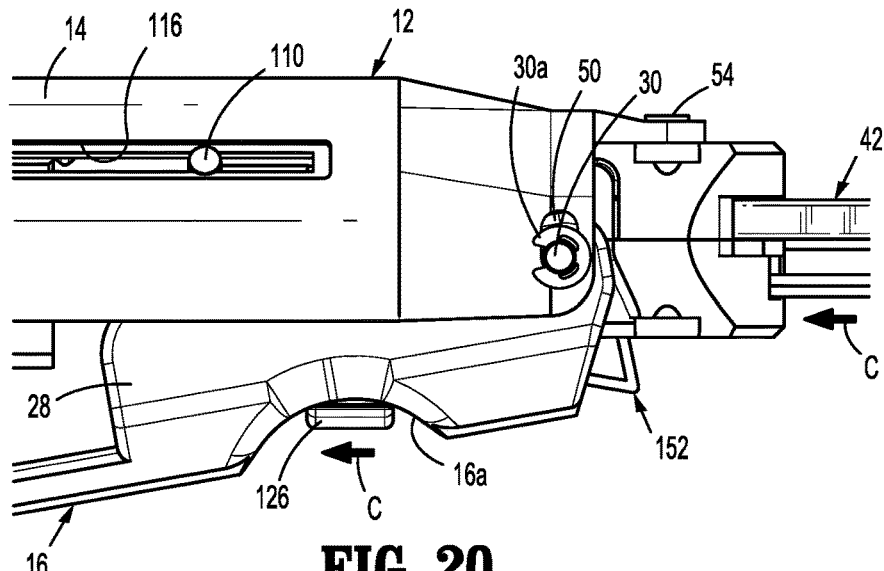
FIG. 20 is a side view of the proximal end of the surgical stapling device shown in FIG. 1 with the surgical stapling device in the open jaw position.
Figure 21:
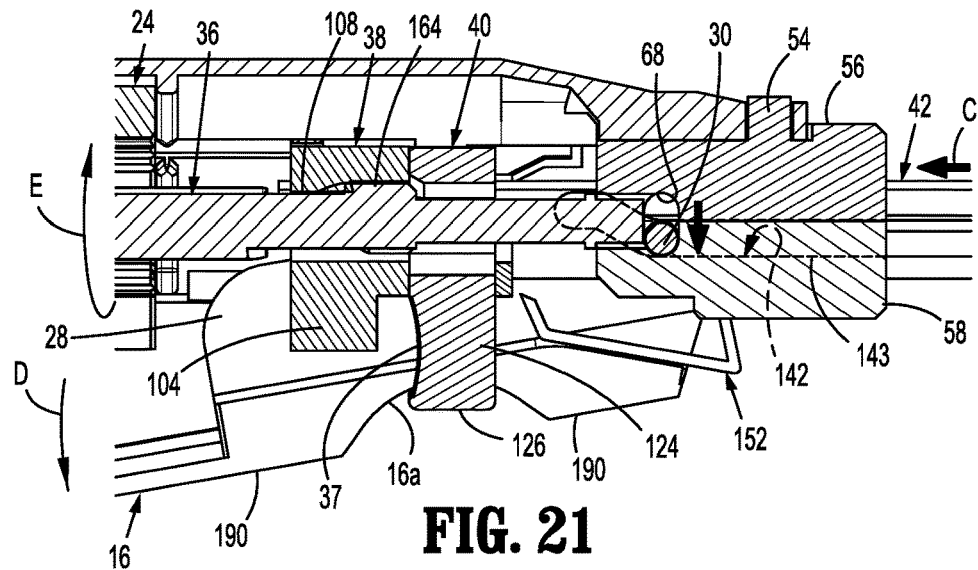
FIG. 21 is a side view of the proximal end of the surgical stapling device shown in FIG. 1 with the housing and barrel removed and the jaws of the surgical stapling device in the open position.

When the push rod 42 is moved distally from its fully retracted position to move the tool assembly 26 from the "parked position" to the "open position", the sled 38 and the clamping member 40 are moved distally about the guide shaft 36 in the direction indicated by arrows "C" in FIGS. 20 and 21. As the clamping member 40 moves distally about the guide shaft 36, the beam 126 of the clamping member 40 moves from a position in engagement with the outer surface 190 of the anvil 16 to a position located within the concavity 16a in the outer surface 190 of the anvil 16, and the pivot pin 30 moves from the short distal linear portion 146 of the cam slot 142 of the push rod 42 through the angled distal portion 144 and into the substantially linear portion 143 of the cam slot 142. As such, the pivot pin 130 is pushed downwardly to lower end of the through bore 50 of the cartridge 14 and the lower end of the elongated slot 68 of the mounting assembly 18 to move the proximal end of the anvil 16 away from the cartridge assembly 16. In addition, the protrusions 125 (FIG. 19A) of the clamping member 40 move off of the ledges 58a of the lower mounting member 58 of the mounting assembly 18 to allow the beam 126 to move away from the outer surface of the anvil 16. In this position, the leaf springs 152 urge the anvil 16 about the pivot member 30 in the direction indicated by arrow "D" in FIG. 21.

As shown in FIG. 21, in the open position of the tool assembly 26, the fins 104 of the sled 38 are positioned proximally of the barrel 24 and thus, are not received within the knife slots 74 of the cartridges 44. As the sled 38 moves about the guide shaft 36 from the "parked position" to the "open position", the cam member 108 engages and moves past the first guide surface 164. As discussed above, the retaining members 110 are secured to the ends of fins 104 and extend through the slots 116 formed in the cartridge housing 14 to prevent rotation of the sled 38 about the guide shaft 36 within the housing 14 of the cartridge assembly 12. As such, when the cam member 108 of the sled 38 engages and moves past the first guide surface 164 of the guide shaft 36, the guide shaft 36 is rotated within the housing 14 to rotate the barrel 24 through a first indexing step as indicated by arrow "E" in FIG. 21. As discussed above, the first guide surface 164 and the cam member 108 are configured to cause the barrel 24 to rotate a new cartridge 44 from a non-active position to an active position in two steps. Thus, where the barrel 24 is formed from three cartridges, each indexing step rotates the barrel 60 degrees such that after two indexing steps, the barrel 24 is rotated 120 degrees to move a fresh cartridge to the active position. It is noted that prior to first use, the surgical stapling device 10 is provided with the barrel in an inactive position in which two cartridges 44 are partially aligned with the anvil 16. As such, during a first firing of the surgical stapling device 10, a cartridge 44 is moved into the active position in a single indexing step. After the first firing of the surgical stapling device 10, two indexing steps are required to position a fresh cartridge 44 into alignment with the anvil 16.

Figure 23:
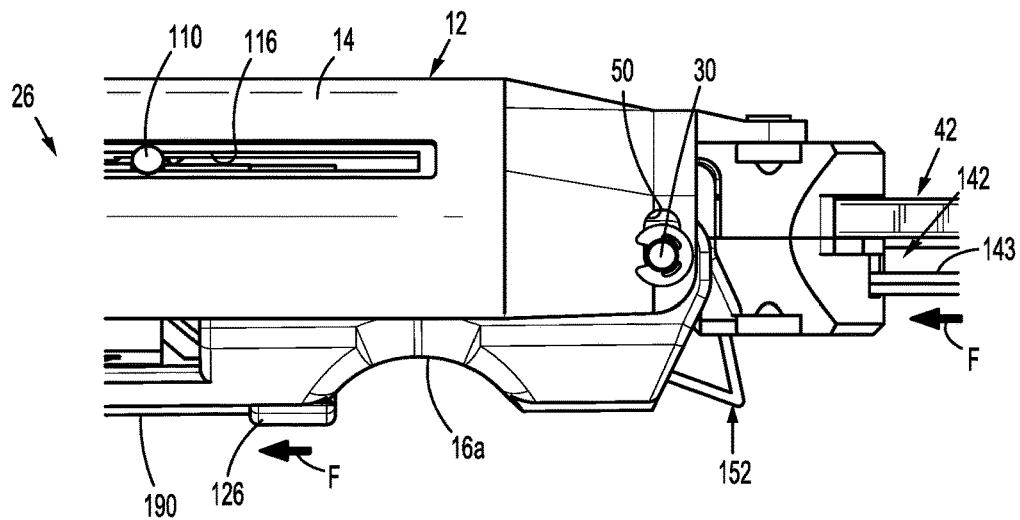
FIG. 23 is a side view of the proximal end of the surgical stapling device shown in FIG. 1 with the surgical stapling device in the clamped position.
Figure 24:
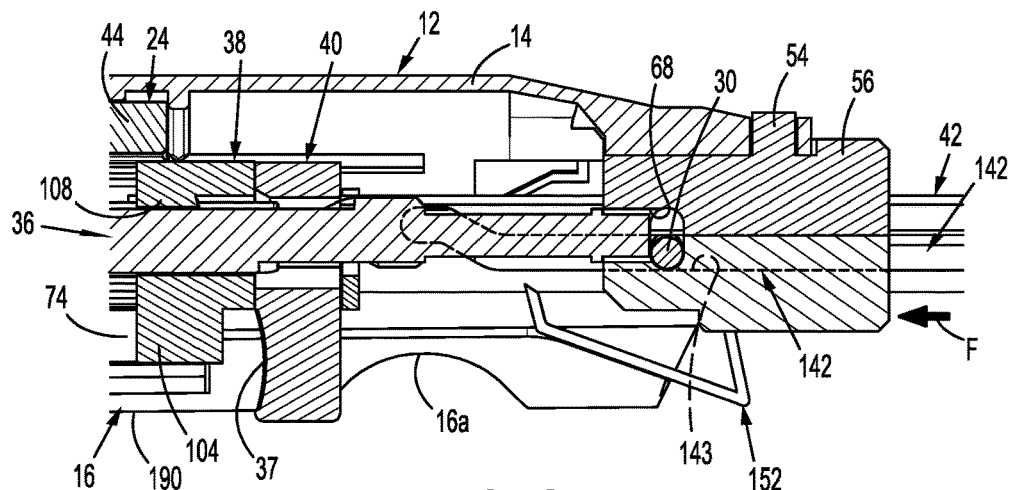
FIG. 24 is a side view of the proximal end of the surgical stapling device shown in FIG. 1 with the housing and barrel removed and the surgical stapling device in the clamped position.
Figure 25:
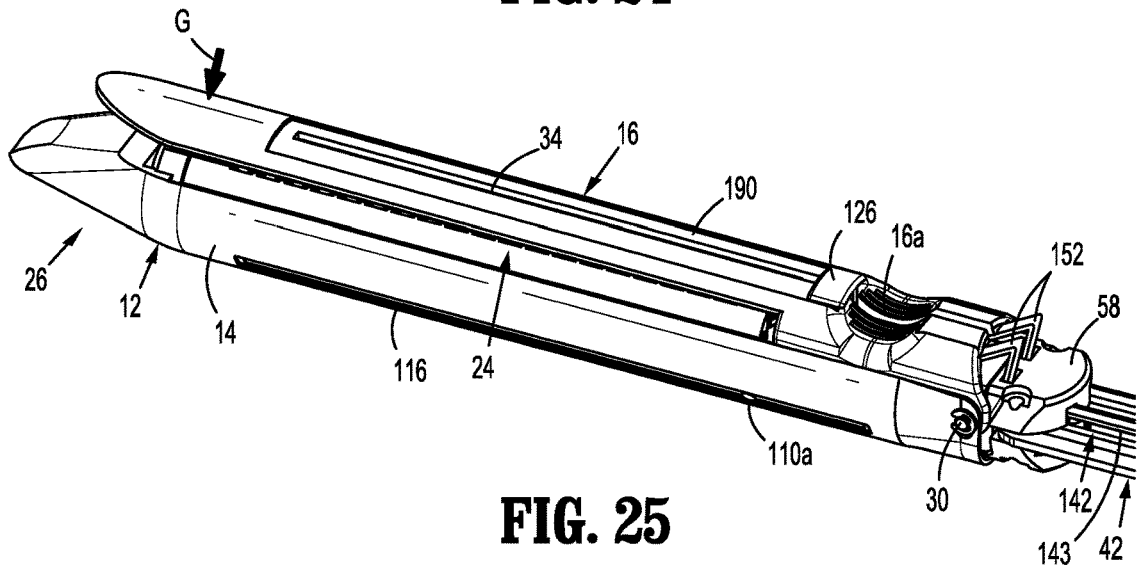
FIG. 25 is a side perspective view of the surgical stapling device shown in FIG. 1 in the clamped position.

Referring to FIGS. 23-25, when the push rod 42 is advanced to move the tool assembly 26 from the "open position" to the "clamped position", the sled 38 and the clamping member 40 are moved distally about the guide shaft 36 in the direction indicated by arrows "F" in FIGS. 23 and 24. As the clamping member 40 moves distally about the guide shaft 36, the beam 126 of the clamping member 40 moves from a position within the concavity 16a to a position in engagement with the outer surface 190 of the anvil 16 at a position distally of the concavity 16a to pivot the anvil 16 in the direction indicated by arrow "G" in FIG. 25 against the urging of the leaf springs 152 to the "clamped position". As the push rod 42 moves distally through the housing 14 of the cartridge assembly 12, the pivot pin 30 moves through the substantially linear portion 143 of the cam clot 142 and is retained in the lower end of the through bore 50 of the cartridge 14 and the lower end of the elongated slot 68 of the mounting assembly 18. In the "clamped position", the fins 104 of the sled 38 enter the knife slots 74 of the cartridges 44 to prevent further rotation of the barrel 24 in relation to the sled 38 within the housing 14 and the pusher fingers 100 of the sled 38 enter the slots 86 (FIG. 17) defined in the active cartridge.

Referring to FIGS. 26 and 27, when the push rod 42 is advanced from the "clamped position" to fire the tool assembly 26, the sled 38 and the clamping member 40 are moved distally about the guide shaft 36 in the direction indicated by arrow "H" in FIGS. 26 and 27. As the sled 38 and the clamping member 40 move distally about the guide shaft 36, the pusher fingers 100 of the sled 38 move into sequential engagement with the backspan 90a of the staples 90 to force the first leg 90b into the staple deforming recesses 32 of the anvil 16 to form D-shaped staples 90 through tissue. Concurrently, the clamping member 40 moves distally through the cartridge assembly 12 such that the knife 37 (FIG. 24) on the vertical strut 124 passes through the knife slot 74 of the active cartridge 44 and the knife slot 34 of the anvil 16 to cut tissue between the rows of staples 90. As the staples 90 are formed and the tissue is cut, the beam 126 of the clamping member 40 moves along the outer surface 190 of the anvil 16 to define a maximum tissue gap between the anvil 16 and the active cartridge during the firing stroke.

Figure 28:
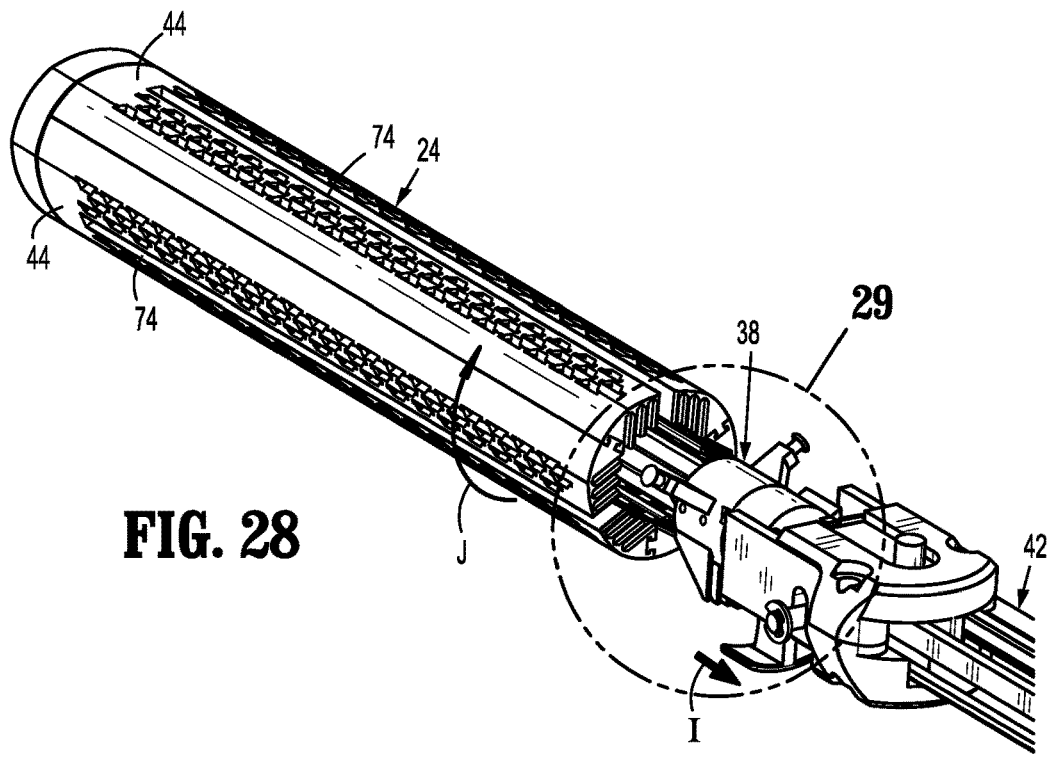
FIG. 28 is a side perspective view of the surgical stapling device shown in FIG. 1 after firing as the push rod is being retracted during a first indexing stage.
Figure 29:
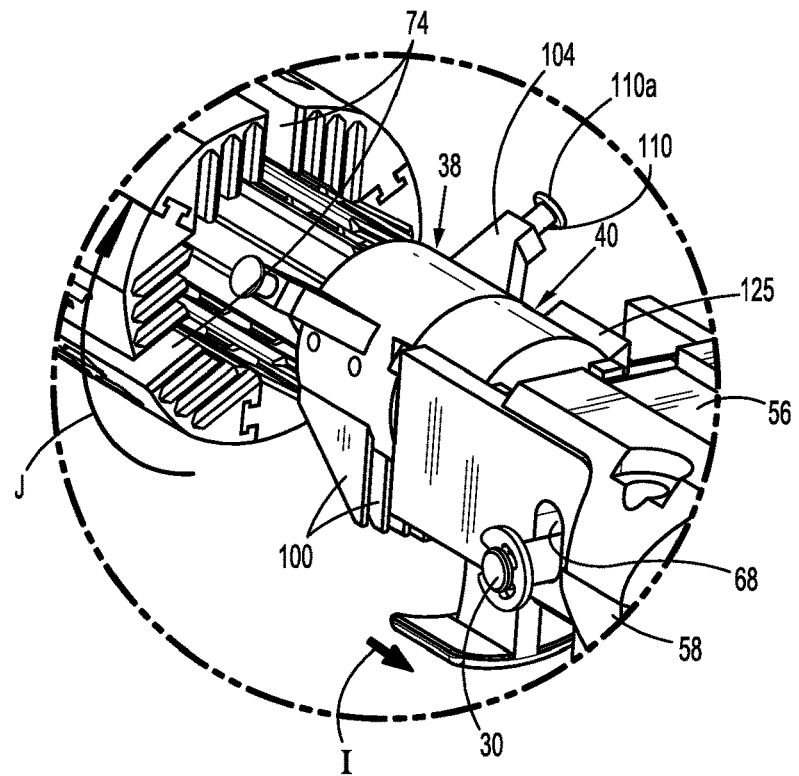
FIG. 29 is an enlarged view of the indicated area of detail shown in FIG. 28.
Figure 30:
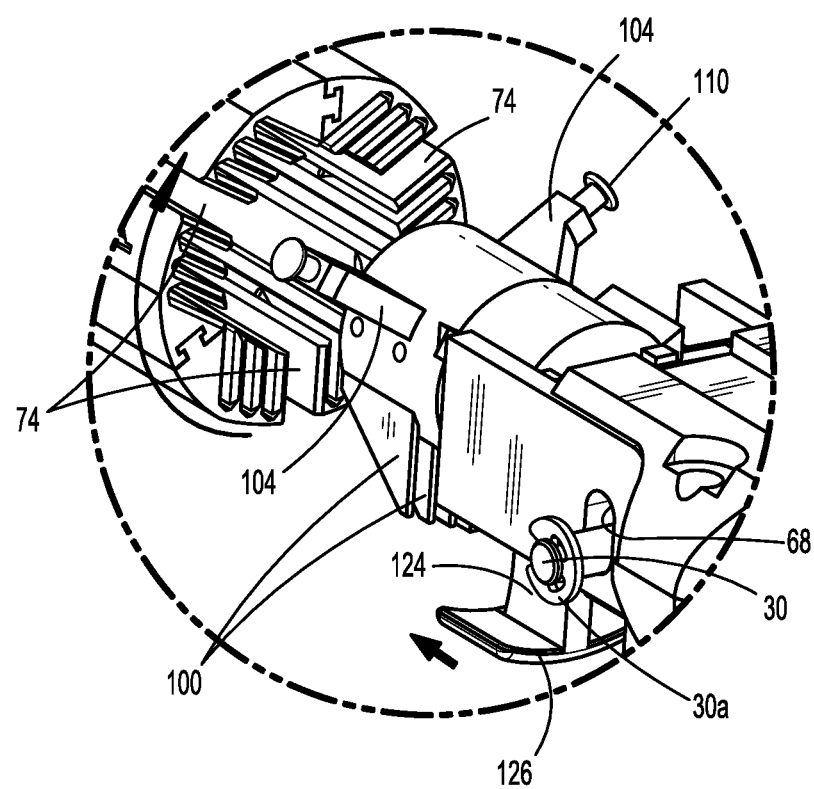
FIG. 30 is an enlarged view of the indicted area of detail shown in FIG. 29 after retraction of the push rod is complete and during a subsequent advancement of the push rod and a second indexing stage.

Referring to FIGS. 28 and 29, after the surgical stapling device is fired, the push rod 42 is moved through a retraction stroke to move the sled 38 and 40 in the direction indicated by arrow "I" in FIGS. 28 and 29 proximally within the cartridge assembly 14 towards a fully retracted position. When the sled 38 is moved to a partially retracted position in which the pusher fingers 100 and the fins 104 are positioned proximally of the barrel 24 and knife slots 74 of the cartridges 44, the cam member 108 (FIG. 24) engages and passes along the second guide surface 166 (FIG. 14) of the guide shaft 36. When the cam member 108 of the sled 38 engages and moves past the second guide surface 164 of the guide shaft 36, the guide shaft 36 is rotated within the housing 14 to rotate the barrel 24 through a second indexing step as indicated by arrow "J" in FIGS. 28 and 29. During the second indexing step, the barrel 24 is rotated to a position in which the spent (fired) active cartridge 44 is moved partially out of alignment with the anvil 16 and a fresh (unfired) cartridge 44 is moved partially into alignment with anvil 16. As discussed above with regard to the first indexing step, the second guide surface 164 and the cam member 108 are configured to cause the barrel 24 to rotate a new cartridge 44 from a non-active position to an active position in two steps. As such, after the surgical stapling device 10 is fired, a new cartridge 44 is rotated halfway to the active position during the second indexing step of the retraction stroke (FIGS. 28 and 29) and, thereafter, rotated to the full active position during movement of the tool assembly 26 from the "parked position" to the "open position" (FIG. 30) during a second actuation of the surgical stapling device 10.

After each firing of the surgical stapling device 10, the barrel 24 will be automatically indexed as described above, to place a fresh cartridge in the active position. Although the barrel 24 is shown to have three cartridges 44 and each indexing step is described as rotating the barrel 24 60 degrees, it envisioned that the barrel 24 may include two or more cartridges and that each indexing step should rotate the barrel 360 degrees divided by 2 times the number of cartridges 44. For example, if the barrel 24 is formed of four cartridges, each indexing step should rotate the barrel 24 360 degrees divided by (2×4) or 45 degrees. As such, the two indexing steps of a surgical stapling device 10 with a barrel 24 formed from four cartridges 44 would rotate the barrel 24 a total of 90 degrees to replace a spent cartridge with an unfired cartridge.

Figure 22:
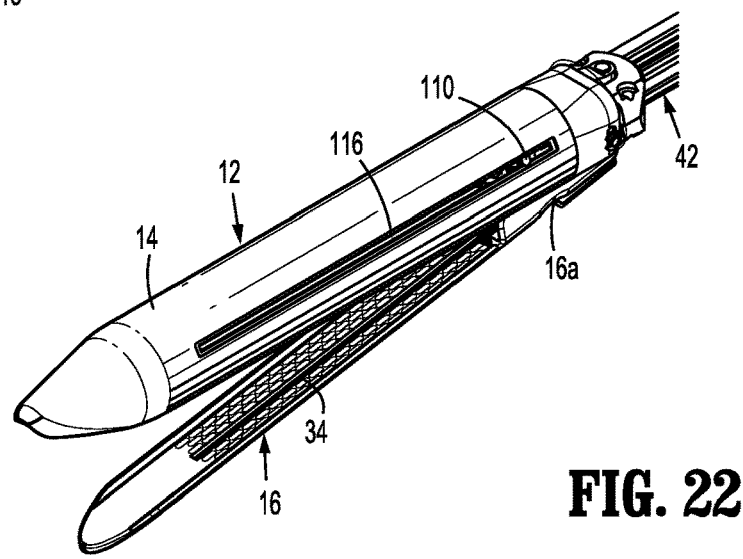
FIG. 22 is a side perspective view of the surgical stapling device shown in FIG. 1 with the jaws of the surgical stapling device in the open position.

The surgical stapling device 10 can be connected to an actuation device such as the actuation device 200 shown schematically in FIG. 31 and described in detail below. Alternately, the surgical stapling device 10 can be connected to other types of actuation devices including manually operated hand held devices, robotically controlled devices, and/or other types of powered or manually actuated devices. The actuation device 200 includes a handle 202 including an actuator button 202a and an adaptor 204 extending distally from the handle 202. In embodiments, the surgical stapling device 10 can be delivered in a packaged state with the tool assembly 26 in an open position and a cartridge in the active position. The surgical stapling device 10 can be loaded onto the adaptor 204 and the adaptor 204 can be secured to the handle 202. A clinician can check the operability of the surgical stapling device 10 by operating the actuation device to open and close the tool assembly 26 and/or articulate the tool assembly in relation to a longitudinal axis defined by the adaptor 204. Prior to insertion of the surgical stapling device 10 through a cannula, the actuation device 200 is operated to move the tool assembly 26 of the surgical stapling device 10 to the "parked position" (FIGS. 18 and 19) to minimize the diameter of the cartridge assembly 12. When this occurs, proximal movement of the sled 38 will move the barrel 24 through an indexing step to move the cartridge from the active position. After the tool assembly 26 is extended through the cannula, the actuation device 200 is operated to move the sled 38 and clamping member 40 distally to move the tool assembly 26 to the "open position" (FIGS. 20-22). As this occurs, the barrel 24 is moved through a second indexing step to move a cartridge back to the active position. Movement of the tool assembly 26 from the "parked position" to the "open position" allows the beam 126 of the clamping member 40 and the anvil 16 to move away from the cartridge assembly 12 to set a proper tissue gap between the anvil 16 and cartridge assembly 12. The status of the tool assembly 10 may be displayed on a LED screen 206 provided on the actuation device 200. With the tool assembly 26 in the open position, the surgical stapling device 10 can be manipulated to position the anvil 16 and cartridge assembly 12 about tissue and the actuation device 200 can be operated to clamp the tissue. Thereafter, the actuation device 200 can be operated to fire the surgical stapling device 10. Each of the cartridges 44 of the barrel 24 may be provided with a chip 208 including an integrated circuit that can be read by a processor 210 in the handle 202 to identify when the cartridge is spent and when the cartridge is fresh or loaded with staples.

After the surgical stapling device 10 is fired, the actuation device 200 can be operated to move the sled 38 and clamping member 40 through a retraction stroke and return the tool assembly 26 to the "open position". At this point, if the clinician requires an additional surgical stapling procedure, the clinician can operate the actuation device 200 to position a fresh cartridge 44 in the active position. In embodiments, the actuation device may include a reload button that can be pressed to fully retract the sled 38 and subsequently readvance the sled 38 to the "open position" to move the barrel 24 through the two indexing steps. If the clinician determines that no further stapling procedure is required, the actuation device 200 can be operated to return the surgical stapling device 10 to the "parked position" to allow for removal of the tool assembly 26 from the cannula. The information stored in the cartridge chips 208 will prevent firing of a spent cartridge.

While several embodiments of the disclosure have been described, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A surgical stapling device comprising:
a housing;
a plurality of cartridges forming a barrel, the barrel being rotatably supported within the housing, each of the plurality of cartridges defining a plurality of staple pockets and supporting a plurality of staples;
an anvil coupled to the housing and movable in relation to the barrel between an open position and a clamped position, each of the plurality of cartridges being movable from an inactive position into an active position in juxtaposed alignment with the anvil when the anvil is in the clamped position; and
a sled movably positioned within the housing through a firing stroke and a retraction stroke, the sled being movable through the barrel during the firing stroke to eject the plurality of staples from a first cartridge of the plurality of cartridges in the active position, the sled being configured such that movement of the sled through at least one of the firing stroke or the retraction stroke causes the barrel to rotate to move a second cartridge of the plurality of cartridges to the active position.

2. The surgical stapling device of claim 1, wherein the plurality of cartridges includes first, second, and third cartridges.

3. The surgical stapling device of claim 1, further including a guide shaft rotatably supported within the housing, the guide shaft being rotatably coupled to the barrel such that rotational movement of the guide shaft causes corresponding rotational movement of the barrel, wherein the guide shaft defines at least one cam channel including at least one guide surface, and the sled includes a cam member, the cam member being movable into engagement with the at least one guide surface to rotate the barrel to move the second cartridge of the plurality of cartridges to the active position.

4. The surgical stapling device of claim 3, wherein the at least one guide surface includes first and second guide surfaces, the cam member being positioned to engage the first guide surface during the firing stroke and to engage the second guide surface during the retraction stroke.

5. The surgical stapling device of claim 4, wherein engagement of the first guide surface of the guide shaft with the cam member of the sled moves the barrel through a first indexing step and engagement of the second guide surface of the guide shaft with the cam member of the sled moves the barrel through a second indexing step, wherein each of the first and second indexing steps rotates the barrel β degrees, wherein β is equal 360 divided by 2x, wherein x is the number of cartridges of the plurality of cartridges.

6. The surgical stapling device of claim 5, wherein the plurality of cartridges includes first, second, and third cartridges and each of the indexing steps rotates the barrel 60 degrees.

7. The surgical stapling device of claim 3, further including a push rod, the push rod having a distal end operatively connected to the sled such that distal movement of the push rod causes distal movement of the sled.

8. The surgical stapling device of claim 5, further including a clamping member operatively connected to the push rod such that distal movement of the push rod causes distal movement of the sled and the clamping member.

9. The surgical stapling device of claim 8, wherein the sled includes a plurality of pusher fingers and each of the plurality of cartridges defines a plurality of slots that communicate with the plurality of staple pockets, the plurality of pusher fingers being positioned to translate through the plurality of slots of the cartridge positioned in the active position to eject the plurality of staples from the cartridge positioned in the active position.

10. The surgical stapling device of claim 9, wherein the clamping member includes a hub positioned about the guide shaft, a vertical strut extending radially outwardly of the hub and a beam supported on an end of the vertical strut and extending transversely of the vertical strut, each of the cartridges of the plurality of cartridges and the anvil defining a knife slot, the vertical strut being positioned to extend through the knife slots of the cartridge in the active position and of the anvil such that the beam is positioned to engage an outer surface of the anvil such that distal movement of the clamping member within the cartridge causes the anvil to move from the open position to the clamped position.

11. The surgical stapling device of claim 10, wherein the sled and the clamping member define longitudinal channels and the push rod includes distally extending rails, wherein the distally extending rails are received within the longitudinal channels of the sled and the clamping member to secure the push rod to the sled and the clamping member.

12. The surgical stapling device of claim 11, wherein the longitudinal channels of the clamping member have a height that is greater than the height of the rails of the push rod such that the clamping member is movable about the guide shaft to move the beam of the clamping member in relation to the plurality of cartridges.

13. The surgical stapling device of claim 12, further including a mounting member supported on a proximal end of the housing, the mounting member being secured to the proximal end of the housing and to the a proximal end of the anvil by a pivot pin.

14. The surgical stapling device of claim 13, wherein the mounting member defines an elongated slot that receives the pivot pin and the housing defines an elongated through bore that receives the pivot pin, the pivot pin being movable within the elongated slot of the mounting member and the elongated through bore of the housing to facilitate movement of the pivot pin and the proximal end of the anvil in relation to the proximal end of the mounting member and the proximal end of the housing.

15. A surgical stapling instrument comprising:
an actuation device; and
a surgical stapling device including:
a housing;
a plurality of cartridges forming a barrel, the barrel being rotatably supported within the housing, each of the plurality of cartridges defining a plurality of staple pockets and supporting a plurality of staples;
an anvil pivotally coupled to the housing, the anvil being movable in relation to the barrel between an open position and a clamped position, each of the plurality of cartridges being sequentially movable from an inactive position to an active position in juxtaposed alignment with the anvil when the anvil is in the clamped position;
a sled movably positioned within the housing to translate through the barrel to eject the plurality of staples from a first cartridge of the plurality of cartridges in the active position;
wherein the sled is configured such that movement of the sled through at least one of a firing stroke or a retraction stroke causes the barrel to rotate to move a second cartridge of the plurality of cartridges to the active position.

16. The surgical stapling instrument of claim 15, wherein the activation device includes a handle and an adaptor supported on a distal end of the handle, the surgical stapling device being supported on a distal end of the adaptor.

17. The surgical stapling instrument of claim 16, wherein the handle is electrically powered.

18. The surgical stapling instrument of claim 17, wherein each of the cartridges of the plurality of cartridges has a chip including an integrated circuit and the handle includes a processor which can read the chips of the plurality of cartridges to identify whether each cartridge of the plurality of cartridges has been fired.

19. The surgical stapling instrument of claim 18, wherein the handle includes an LED screen for indicating the current status of the surgical stapling device.

* * * * *